(12) United States Patent
Burow et al.

(10) Patent No.: US 7,390,458 B2
(45) Date of Patent: Jun. 24, 2008

(54) HIGH THROUGHPUT PROCESSING SYSTEM AND METHOD OF USING

(75) Inventors: Kristina Marie Burow, Cardiff, CA (US); Jeremy S. Caldwell, Del Mar, CA (US); Robert Charles Downs, La Jolla, CA (US); Scott Allan Lesley, San Diego, CA (US); James Kevin Mainquist, San Diego, CA (US); Andrew J. Meyer, San Diego, CA (US); Daniel G. Sipes, Bethel Island, CA (US); Mark Richard Weselak, San Diego, CA (US)

(73) Assignee: IRM LLC, Hamilton (BM)

( * ) Notice: Subject to any disclaimer, the term of this patent is extended or adjusted under 35 U.S.C. 154(b) by 239 days.

(21) Appl. No.: 09/981,313

(22) Filed: Oct. 15, 2001

(65) Prior Publication Data

US 2002/0090320 A1 Jul. 11, 2002

Related U.S. Application Data

(60) Provisional application No. 60/240,361, filed on Oct. 13, 2000.

(51) Int. Cl.
*G01N 35/10* (2006.01)
*G01N 21/01* (2006.01)
*G01N 33/50* (2006.01)
*B25J 15/00* (2006.01)
*B01L 3/02* (2006.01)

(52) U.S. Cl. .................... 422/63; 73/863.32; 73/864.01; 73/864.91; 414/222.13; 414/226.05; 414/741; 422/63; 422/65; 422/67; 422/100

(58) Field of Classification Search ............. 422/63–65, 422/67, 100–104; 73/863.32, 864.01, 864.91; 414/222.13, 226.05, 741
See application file for complete search history.

(56) References Cited

U.S. PATENT DOCUMENTS 3,193,358 A * 7/1965 Baruch .................... 422/64

(Continued)

FOREIGN PATENT DOCUMENTS

EP 0 355 866 2/1990

(Continued)

OTHER PUBLICATIONS

Bentley, D. R. et al, Genomics 1992, 12, 534-541.*

(Continued)

*Primary Examiner*—Arlen Soderquist
(74) *Attorney, Agent, or Firm*—Timothy L. Smith; Genomics Institute of the Novartis Research Foundation

(57) ABSTRACT

Briefly, the present invention provides a system and method for high throughput processing using sample holders. The system has a plurality of work perimeters, with a rotational robot preferably associated with each work perimeter. At least one transfer station area is provided between adjacent work perimeters to facilitate robotic transfer of sample holders from one work perimeter to another area. Each work perimeter typically includes a plurality of defined station locations, with each station location positioned to be accessible by the robot associated with that area. In addition, each station location is typically configured to receive a device, such as an automated instrument or a holding nest. Device components are arranged at selected station locations according to specific application requirements to provide a flexible, robust, reliable, and accurate high throughput processing system.

73 Claims, 18 Drawing Sheets

U.S. PATENT DOCUMENTS

| | | | |
|---|---|---|---|
| 3,568,735 A * | 3/1971 | Lancaster | 141/238 |
| 3,787,185 A * | 1/1974 | Rohrbaugh et al. | 422/64 |
| 3,824,674 A | 7/1974 | Inoyama et al. | |
| 3,883,305 A * | 5/1975 | Hoskins et al. | 422/65 |
| 4,234,538 A * | 11/1980 | Ginsberg et al. | 422/64 |
| 4,315,891 A * | 2/1982 | Sakurada | 422/64 |
| 4,459,265 A * | 7/1984 | Berglund | 422/64 |
| 4,465,416 A | 8/1984 | Burkhalter et al. | |
| 4,616,414 A | 10/1986 | Cushman | |
| 4,662,811 A | 5/1987 | Hayden | |
| 4,714,865 A | 12/1987 | Chin et al. | |
| 4,715,637 A | 12/1987 | Hosoda et al. | |
| 4,731,225 A * | 3/1988 | Wakatake | 422/65 |
| 4,774,055 A * | 9/1988 | Wakatake et al. | 422/64 |
| 4,835,707 A * | 5/1989 | Amano et al. | 700/266 |
| 4,894,103 A | 1/1990 | Bailey | |
| 4,900,078 A | 2/1990 | Bloch | |
| 4,906,433 A * | 3/1990 | Minekane | 422/64 |
| 4,923,054 A | 5/1990 | Ohtani et al. | |
| 4,927,545 A * | 5/1990 | Roginski | 210/745 |
| 4,944,650 A | 7/1990 | Matsumoto et al. | |
| 4,952,115 A | 8/1990 | Ohkase | |
| 4,965,049 A * | 10/1990 | Lillig et al. | 422/68.1 |
| 4,976,484 A | 12/1990 | Nomaru et al. | |
| 5,022,695 A | 6/1991 | Ayers | |
| 5,061,144 A | 10/1991 | Akimoto et al. | |
| 5,062,756 A | 11/1991 | McArthur et al. | |
| 5,087,423 A * | 2/1992 | Ishibashi | 422/67 |
| 5,100,285 A | 3/1992 | Wagner | |
| 5,162,047 A | 11/1992 | Wada et al. | |
| 5,164,318 A * | 11/1992 | Sato et al. | 435/286.4 |
| 5,183,638 A * | 2/1993 | Wakatake | 422/64 |
| 5,192,106 A | 3/1993 | Kaufman | |
| 5,201,501 A | 4/1993 | Fassler | |
| 5,206,171 A * | 4/1993 | Dillon et al. | 435/286.3 |
| 5,207,986 A * | 5/1993 | Kadota et al. | 422/65 |
| 5,215,714 A * | 6/1993 | Okada et al. | 422/64 |
| 5,253,911 A | 10/1993 | Egan et al. | |
| 5,308,222 A | 5/1994 | Bacchi et al. | |
| 5,328,224 A | 7/1994 | Jacobsen et al. | |
| 5,417,922 A * | 5/1995 | Markin et al. | 422/65 |
| 5,437,838 A * | 8/1995 | DeMoranville et al. | 422/67 |
| 5,441,699 A | 8/1995 | So et al. | |
| 5,443,791 A * | 8/1995 | Cathcart et al. | 422/65 |
| 5,445,486 A | 8/1995 | Kitayama et al. | |
| 5,512,441 A | 4/1996 | Ronai | |
| 5,541,485 A | 7/1996 | Teichmann et al. | |
| 5,543,022 A | 8/1996 | Nguyen et al. | |
| 5,549,444 A | 8/1996 | Debuit | |
| 5,561,742 A | 10/1996 | Terada et al. | |
| 5,585,068 A * | 12/1996 | Panetz et al. | 422/64 |
| 5,592,289 A * | 1/1997 | Norris | 356/244 |
| 5,614,415 A * | 3/1997 | Markin | 436/48 |
| 5,651,823 A * | 7/1997 | Parodi et al. | 118/500 |
| 5,669,644 A | 9/1997 | Kaihotsu et al. | |
| 5,697,480 A | 12/1997 | Herbermann et al. | |
| 5,700,046 A | 12/1997 | Van Doren et al. | |
| 5,778,742 A | 7/1998 | Stuart | |
| 5,810,935 A | 9/1998 | Lee et al. | |
| 5,824,485 A * | 10/1998 | Thompson et al. | 435/6 |
| 5,858,671 A * | 1/1999 | Jones | 435/6 |
| 5,863,086 A | 1/1999 | Christenson | |
| 5,870,488 A | 2/1999 | Rush et al. | |
| 5,871,248 A | 2/1999 | Okogbaa et al. | |
| 5,876,670 A * | 3/1999 | Mitsumaki et al. | 422/65 |
| 5,889,174 A * | 3/1999 | Warren et al. | 536/23.71 |
| 5,902,549 A * | 5/1999 | Mimura et al. | 422/65 |
| 5,928,952 A | 7/1999 | Hutchins et al. | |
| 5,944,476 A | 8/1999 | Bacchi et al. | |
| 5,945,798 A | 8/1999 | Stagnitto et al. | |
| 5,972,295 A * | 10/1999 | Hanawa et al. | 422/65 |
| 5,981,200 A | 11/1999 | Tsien et al. | |
| 5,985,214 A | 11/1999 | Stylli et al. | |
| 5,993,746 A * | 11/1999 | Priha et al. | 422/104 |
| 6,012,895 A | 1/2000 | Smith et al. | |
| 6,015,174 A | 1/2000 | Raes et al. | |
| 6,024,204 A | 2/2000 | van Dyke, Jr. et al. | |
| 6,024,925 A * | 2/2000 | Little et al. | 422/100 |
| 6,045,755 A | 4/2000 | Lebl et al. | |
| 6,056,106 A | 5/2000 | van Dyke, Jr. et al. | |
| 6,063,339 A | 5/2000 | Tisone et al. | |
| 6,063,579 A * | 5/2000 | Bevirt et al. | 435/6 |
| 6,071,748 A * | 6/2000 | Modlin et al. | 436/174 |
| 6,100,030 A * | 8/2000 | McCasky Feazel et al. | 435/6 |
| 6,116,848 A | 9/2000 | Thomas et al. | |
| 6,132,685 A * | 10/2000 | Kercso et al. | 422/104 |
| 6,284,113 B1 | 9/2001 | Bjornson et al. | |
| 6,305,898 B1 | 10/2001 | Yamagishi et al. | |
| 6,322,119 B1 | 11/2001 | Schmidt et al. | |
| 6,323,035 B1 * | 11/2001 | Kedar et al. | 436/43 |
| 6,409,241 B1 | 6/2002 | Hughes et al. | |
| 6,416,719 B1 * | 7/2002 | Fawcett et al. | 422/104 |
| 6,429,016 B1 * | 8/2002 | McNeil | 436/47 |
| 6,467,827 B1 | 10/2002 | Ardezzone | |
| 6,474,712 B1 | 11/2002 | Govzman et al. | |
| 6,578,893 B2 | 6/2003 | Soucy et al. | |
| 6,592,324 B2 | 7/2003 | Downs et al. | |
| 6,664,048 B1 * | 12/2003 | Wanker et al. | 435/6 |
| 6,932,557 B2 | 8/2005 | Downs et al. | |
| 7,014,235 B1 | 3/2006 | Ostwald | |
| 7,140,655 B2 | 11/2006 | Kesil et al. | |

FOREIGN PATENT DOCUMENTS

| | | |
|---|---|---|
| EP | 0 915 341 | 5/1999 |
| EP | 0 975 009 | 1/2000 |
| GB | 2185458 | 7/1987 |
| JP | 03-012554 | 1/1991 |
| JP | 11-227941 | 8/1999 |
| WO | WO 98/40159 | 9/1998 |
| WO | WO 98/52047 A1 | 11/1998 |
| WO | WO 00/17643 | 3/2000 |

OTHER PUBLICATIONS

Olsen, A. S. et al, Biotechniques 1993, 14, 116-117, 120-123.*
Meier-Ewert, S. et al, Nature 1993, 361, 375-376.*
Maier, E. et al, Journal of Biotechnology 1994, 35, 191-203.*
Maier, E. et al, Drug Discovery Today 1997, 2, 315-324.*
Lueking, A. et al, Analytical Biochemistry 1999, 270, 103-111.*
Drmanac, R. et al, Electrophoresis 1992, 13, 566-573.*
Whigan, D. B. et al, Journal of Chromatography B 1995, 664, 357-363.*
Stubbs, R. J. et al, Journal of Chromatography B 1995, 670, 279-285.*
Tsina, I. et al, Journal of Chromatography B 1996, 675, 119-129.*
Brandt, D. W., Journal of Biomolecular Screening 1997, 2, 111-116.*
Callejas, S. L. et al, Journal of Chromatography B 1998, 718, 243-250.*
Bancroft, D. R. et al, Methods in Microbiology 1999, 28, 67-82.*
Dufresne, C., Journal of Automated Methods & Management in Chemistry 2000, 22, 175-179.*
Brodack, J. W. et al, Journal of Nuclear Medicine 1986, 27, 714-721.*
"Genome on a Chip", Genomics Group, web site: w95vol.neuro.chop.edu/vcheung/projects.htm, pp. 1-6.

* cited by examiner

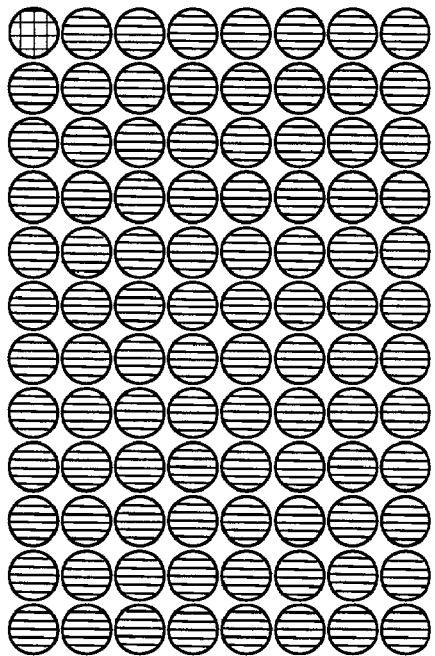
Fig. 11A
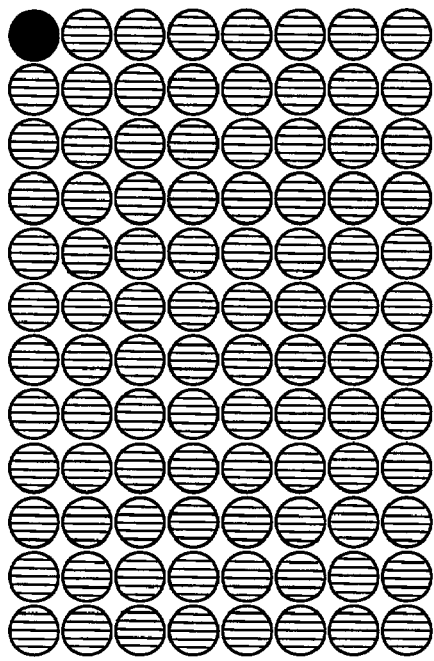
Fig. 11B
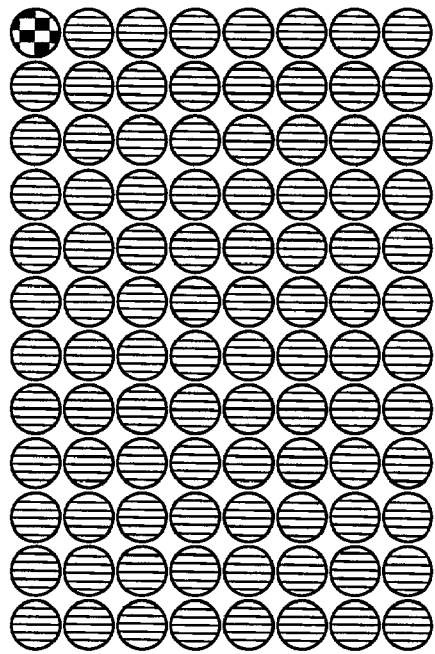
Fig. 11C
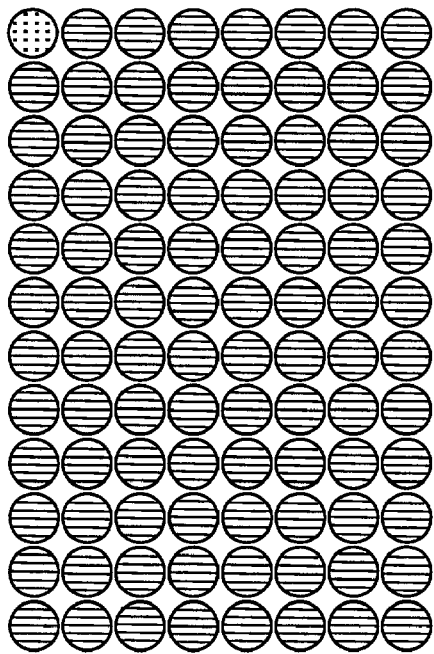
Fig. 11D
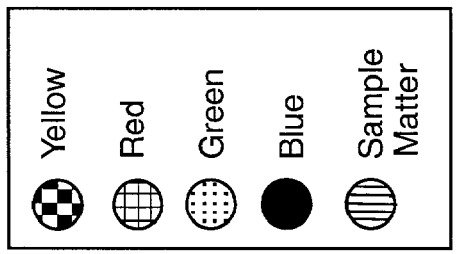

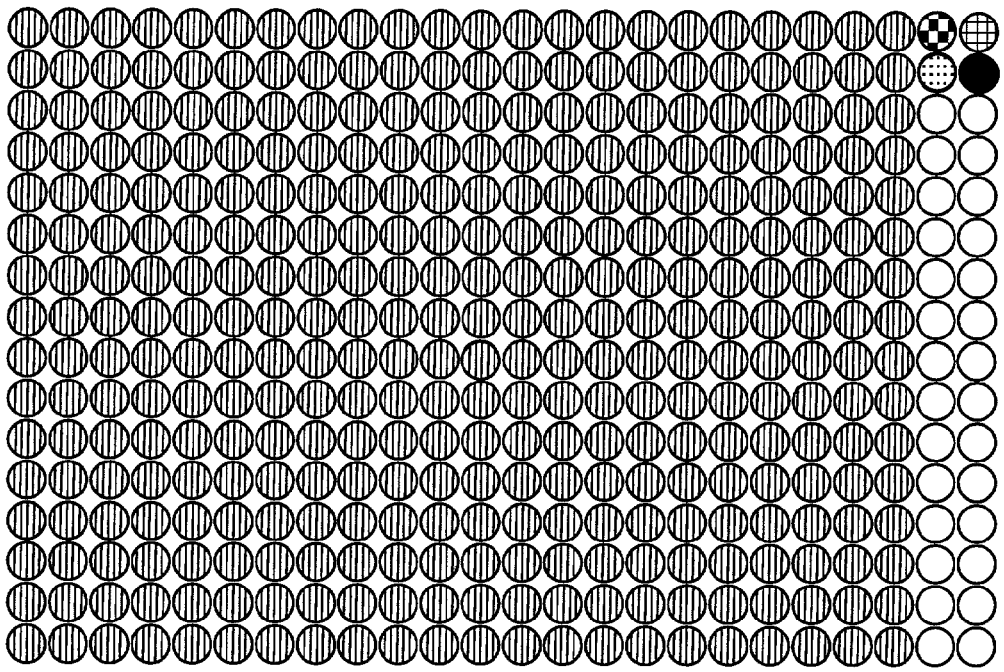
Fig. 12A
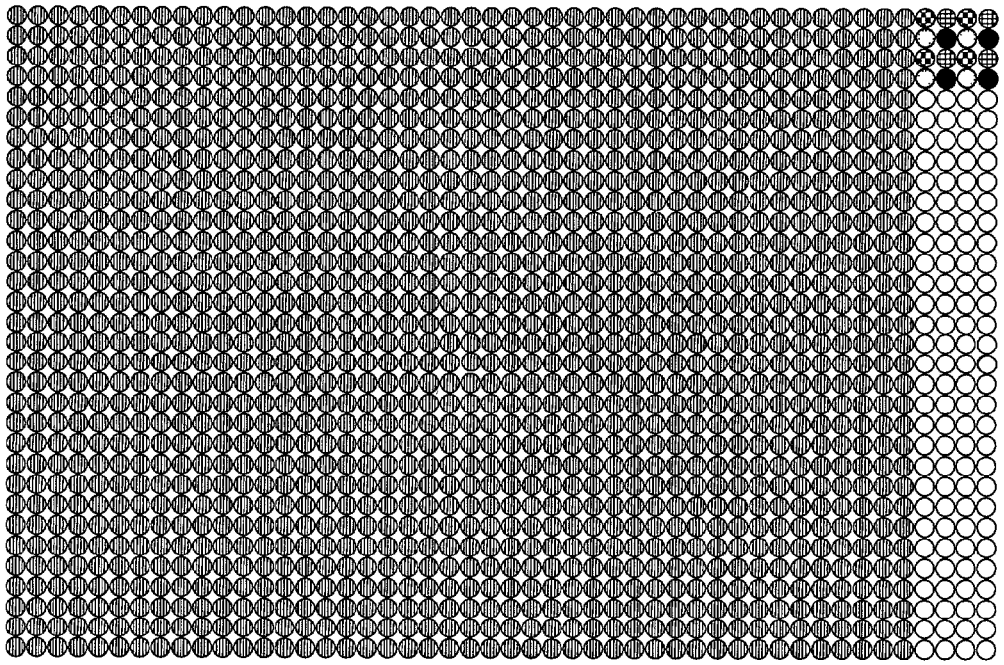
Fig. 12B
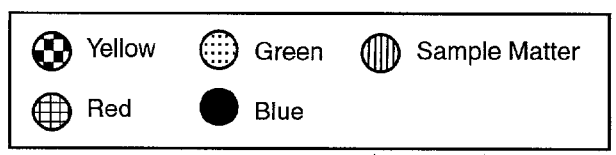

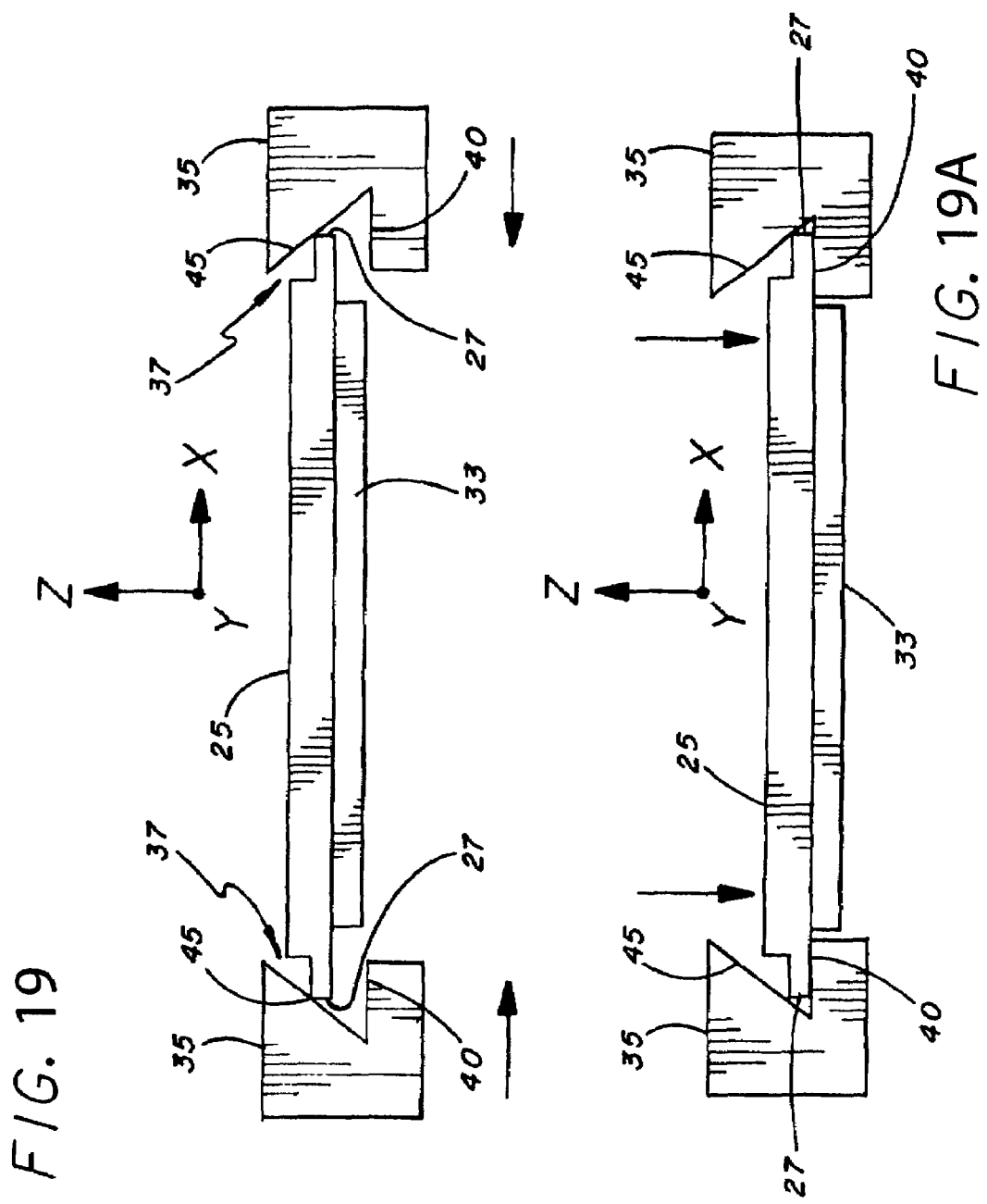

HIGH THROUGHPUT PROCESSING SYSTEM AND METHOD OF USING

CROSS REFERENCE TO RELATED APPLICATIONS

Pursuant to 35 U.S.C. §§ 119, 120, and any other applicable statute or rule, the present application claims benefit of and priority to U.S. Patent Application Ser. No. 60/240,361, filed Oct. 13, 2000, entitled "High Throughput Processing System and Methods of Using," and the PCT application entitled "High Throughput Processing System and Methods of Using," filed Oct. 15, 2001, PCT/US01/32454, the disclosures of which are incorporated herein by reference in their entirety for all purposes.

COPYRIGHT NOTIFICATION

Pursuant to 37 C.F.R. 1.71(e), a portion of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

Automated processing systems are useful in many applications and fields. For example, automated laboratory systems are used in biotechnology and biomedical industries, e.g., for producing large numbers of samples and screening these samples for a desired property. Such samples include, but are not limited to, chemicals, cells, cell extracts, or genetic material such as cDNA, retroviruses, or anti-sense oligonucleotides. To facilitate faster processing, samples are typically processed together on a multi-well specimen plate, such as a 384 or 1,536 well plate.

Automated systems using specimen plates generally provide faster processing of samples as compared to manual processes. High throughput automated systems typically involve rapid, repetitive manipulations of individual elements. One deficiency in existing technology is that as processing throughputs increase there is a degradation of reliability.

One example of an automated processing system is found in U.S. Pat. No. 5,985,214, which relates to a system having several workstations. A conveyor transport moves specimen plates holding samples between the workstations. Accordingly, the specimen plate moves in a linear fashion from a first processing workstation to the next sequential processing workstation. To move to any workstation, a specimen plate is first retrieved from a central storage rack, and then transported down a long linear track until the plate reaches one of the several workstations. When the plate is at the desired workstation, the plate leaves the first linear track and is placed on a second orthogonal linear track that presents the plate to an automated instrument. This system, however, suffers from a lack of flexibility. The plates must proceed in a linear fashion along the entire track, thus limiting throughput. Further, once the rack, workstation, and cooperating transports are in place, it is difficult to reconfigure the system. In addition, samples in the specimen plates are subjected to an open and unprotected environment for an extended period of time as the plates move from the sample racks to the workstations. Thus, the samples may become impermissibly dry or contaminated.

Another known automated processing system is described in U.S. Pat. No. 5,928,952, which relates to a system having a series of processing units arranged to sequentially receive specimen plates holding samples or products. In this system, each individual unit performs a specific task using the specimen plates. Further, each unit has an associated robotic device for receiving a plate from an adjacent unit. The system uses plural robots to perform automated process having several steps. For example, for a unit performing a step in the process, a robot associated with the unit retrieves a specimen plate from the previous unit and moves the specimen plate to the processing position in the unit. When the unit has completed its step, the robot moves the specimen plate to where the next robot can retrieve the plate. In such a manner, the system is cumbersome to operate in a process having many steps and using several different workstations.

Disadvantageously, current high throughput processing systems are limited to unidirectional workflow and inflexible testing regimes. For example, once the testing samples are delivered to a workstation in U.S. Pat. No. 5,985,214 or the interchangeable unit in U.S. Pat. No. 5,928,952, the samples proceed inexorably from one workstation to the next workstation in only one direction. Current systems do not allow for a sample to proceed, for example, from an assaying step, to a dispensing step, and then back to the previous assaying step. Instead, an entirely new workstation must be built subsequent to the dispensing step in order to perform the assay step that was provided two workstations ago. As each workstation is capable of performing only one function, every additional step in current systems involves adding another robot and another workstation, thereby entailing additional alignment, integration and calibration with the overall system.

Therefore, there exists a need for an efficient automated processing system such as a high throughput processing system that is accurate, reliable, and flexible. The demand for high throughput systems with decreased reconfiguration needs that are prone to less contamination and can process samples multi-directionally within the system is as yet unmet. The present invention provides improved high throughput processing systems that fulfill these needs and many others that will be apparent upon complete review of the following disclosure.

SUMMARY OF THE INVENTION

The present invention methods and systems for high throughput processing, e.g., flexible, efficient, and robust high throughput processing, such as screening of chemical and/or biochemical libraries. Typically, the systems comprise work perimeters that are configured for optimum flexibility while retaining an efficient and precise system. The systems optionally perform assays of at least about 100,000 samples in about one day, at least about 350,000 samples in about one day, or at least about 700,000 samples in about one day.

In one embodiment, a high throughput processing system is provided. The system typically comprises a plurality of rotational robots, wherein each of the rotational robots has a reach which defines a work perimeter associated with that rotational robot. Typically, at least one device is associated with each of the work perimeters, and at least one of the work perimeters has two or more devices exclusively within the reach of the associated rotational robot. In addition, one or more transfer stations is associated with at least a first work perimeter and a second work perimeter, for transferring samples or sample holders from the first work perimeter to the second work perimeter. The system can transfer samples along a multi-directional path, or a non-sequential or non-linear path.

The systems also typically comprise a plurality of sample holders, e.g., comprising a plurality of test samples or compounds, which sample holders are transported between devices and work perimeters during operation of the system. Typical sample holders include, but are not limited to, specimen plates, multiwell plates (1536-well plates, 384-well plates, and/or 96-well plates), petri dishes, test tube arrays, vials, crucibles, flasks, reaction vessels, slides, and the like.

In some embodiments, the sample holders comprise one or more lids. An example lid of the invention comprises a cover having a top surface, a bottom surface, and a side. An alignment protrusion extends from the side of the cover, e.g., positioned to cooperate with an alignment member of the multiwell plate. In addition, a sealing perimeter is positioned on the bottom surface of the cover. The alignment protrusion facilitates aligning the lid to the plate so that a seal is compressibly received between the sealing perimeter and a sealing surface of the multiwell plate. The lids are, in some embodiments, constructed of a heavy material such as stainless steel. A de-lidding station is also optionally incorporated into the systems of the invention, at which station a lid is removed from a sample holder.

Samples optionally screened or processed in the present systems comprise chemical or biochemical compounds, nucleic acids, peptides, polypeptides, proteins, carbohydrates, cells, serum, phage particles, virions, enzymes, cell extracts, lipids, antibodies, and the like. For example, one or more library of cDNA molecules, antisense nucleic acids, double-stranded RNA molecules, or gene regulatory regions, e.g., operably linked to a reporter gene, are optionally screened in the present systems. Regulatory regions in such libraries are optionally derived from genes that are differentially expressed in a cell depending upon the presence or absence of a particular stimulus. Combinatorial libraries of chemical compounds are also optionally screened using the present systems.

In addition to the samples described above, a second set of sample holders are optionally assay holders that comprise containers and/or reagents for conducting one or more assay. The assay holders optionally comprise one or more components of an assay, in which a test sample is added to the assay containers, e.g., from a first set of sample holders, to determine the effect of the test samples on the assay. Assays, e.g., cell based assays, performed in the present systems include, but are not limited to, a G-protein coupled receptor assay, a kinase assay, a protease assay, a phosphatase assay, a transcription assay, and the like.

The rotational robots, e.g., between about 2 and about 10 robots, of the system optionally each comprise one or more grippers configured to transport the sample holders, which grippers optionally comprise a sensor structured to determine a location of the gripper apparatus relative to the object. In addition, the grippers optionally comprise a deflectable member structured to couple the gripper apparatus to a robotic member, which deflectable member is structured to deflect when the gripper apparatus contacts an item with a force greater than a preset force. In some embodiments, at least one of the rotational robots includes a grasping mechanism that comprises moveably coupled arms that are structured to grasp an object, wherein at least one arm comprises a pivot member having a support surface to support the object and a height adjusting surface that pushes the object into contact with the support surface when the arms grasp the object.

Devices for use in the system are typically selected from a fluid transfer device, e.g., a pin tool, a syringe, a pump or the like, a mixer, an incubator, a storage compartment, a thermocycler, a plate carousel, an automatic sample processor, a detector, a replating station, and the like.

A fluid transfer device is optionally used as a device of the invention. The fluid transfer devices can, for example, transfer an aliquot of a test sample from a sample holder that comprises test samples to an assay sample holder in which an assay is to be performed. Fluid transfer devices can also dispense fluids, such as reagents, etc., from a reservoir into one or more sample holders. The assay holders typically comprise one or more of living cells, cell extracts, nucleic acids, polypeptides, antibodies, or chemicals, e.g., for a biochemical, chemical, biological, microbiological, or cell-based assay.

Fluid transfer devices of the invention optionally comprise an array of receptacles, e.g., 96 or 384 receptacles such as syringes, arranged such that outlets of the receptacles are aligned with a plurality of wells of one or more multiwell plate. In another embodiment, a fluid transfer device aspirates a volume of sample into one or more of the receptacles from a well of a multiwell plate which is aligned with the outlet of the receptacle. The device then typically returns a substantial portion of the volume of the aspirated sample to the well of the multiwell plate, the returned volume of the liquid being less than the aspirated volume so that a volume of sample is retained in the receptacle. A portion of the retained volume of sample is then dispensed, e.g., into a well of a second multiwell plate; and any remaining volume of retained liquid is optionally discarded. When a pin tool is used as a fluid transfer device, the system can further comprises one or more wash stations in which the pins are washed between transfers of fluid from one multiwell plate to another by the pin tool. Typically, the fluid transfer devices of the invention do not comprise disposable pipette tips.

The systems of the invention can include storage compartments that provide storage capacity for at least about 350,000 samples. In some embodiments, storage is provided for at least about 700,000 samples, or at least about 1,400,000 samples. An example storage compartment has a housing that includes a plurality of doors, which doors close at least one opening disposed through at least one surface of the housing. At least one movable shelf is disposed within the housing, which shelf is capable of aligning with the opening. Each of the plurality of doors is typically independently accessible by the rotational robot.

Detectors included in the systems of the invention can include but are not limited to, a fluorescence detector, a spectrophotometric detector, a luminescence detector, a phosphorescence detector, an X-ray detector, a radio-frequency detector, a bar code reader, a mass spectrometer, a radioactivity detector, an optical detector, and the like. In some embodiments, the detector comprises a camera which records images, e.g., digital images, of the assay results. The resulting images are analyzed, e.g., at a later date or time, to determine assay results which indicate a desired effect of a test sample.

In some embodiments, the sample holders comprise multiwell plates and one or more of the devices of the system comprise a positioning device. The positioning device typically comprises at least a first alignment member that is positioned to contact an inner wall of the multiwell plate when the multiwell plate is in a desired position on the device. The positioning device further comprises a pusher that can move the multiwell plate in a first direction to bring a first inner wall of the multiwell plate into contact with one or more of the alignment members.

The high throughput processing systems of the invention can also include a controller operably coupled to the system. The controller typically directs transport of the sample holders between one or more of the work perimeters or between one or more of the devices. Operator instructions to program and direct the system through the controller can optionally be received through a graphical user interface.

In another aspect, the present invention provides methods of defining a process for operation, e.g., on a high throughput processing system as provided above. The methods typically comprise creating a plurality of device steps, wherein each device step instructs one of the one or more devices in the high throughput processing system. A plurality of move steps are also created. Each move step instructs at least a first member of the plurality of rotational robots, e.g., to move one or more of the sample holders to one of the one or more devices. The device steps and the move steps are then arranged into a step list, the step list defining an order for performing the process.

In another aspect, the present invention provides a method of transferring a plurality of samples from two or more members of a first set of multiwell plates to a member of a second set of multiwell plates. The method typically comprises providing the two or more members of the first set of multiwell plates, which members comprise the plurality of samples. In addition, each member comprises a marker in at least a first well of the multiwell plate. The plurality of samples and the marker are then transferred from the members of the first set of multiwell plates to a member of the second set of multiwell plates; and the location of the marker from each member of the first set of multiwell plates in the member of the second set of multiwell plates is determined. Determining the location of the markers typically comprises visual monitoring or fluorescent monitoring. For example, each member of the first set of multiwell plates typically comprises a marker which differs from the marker in other members of the first set of multiwell plates, e.g., the markers comprise colored dyes and the markers differ in the color of the dye and/or the markers comprise fluorescent dyes and differ in the concentrations of the fluorescent dyes.

Typically the members of the second set of multiwell plates have a number of wells that is a whole number multiple of the number of wells in the members of the first set of multiwell plates. For example, the samples and markers can be transferred from four members of the first set of multiwell plates to one member of the second set of multiwell plates. The first set of multiwell plates can be, for example, 96-well plates and the second set of multiwell plates are 384-well plates. Alternatively, the first set of multiwell plates are 384-well plates or 96-well plates and the second set of multiwell plates comprises 1536-well plates. The methods are particularly useful for use with a high throughput processing system as described herein. Such systems can have, for example, one type of plate in one work perimeter and a plate having a different well density in another work perimeter. The plating methods of the invention allow one to ascertain whether samples are transferred correctly from one plate to another having a different well density. Each of these systems and methods are described in more detail below.

BRIEF DESCRIPTION OF THE FIGURES

FIGS. 11A-D illustrate four 96-well multiwell plates each comprising a unique marker useful in a replating procedure.

FIGS. 12A and 12B illustrate higher well density plates that contain the contents of the four 96 well plates in FIG. 11. FIG. 12A illustrates a 384-well plate and FIG. 12B illustrates a 1536-well plate. Both of the higher well density plates comprise the markers included in the 96-well plates to indicate the orientation in which the lower well density plates were transferred to the higher well density plates.

FIG. 13A provides a top view, FIG. 13B provides a side view, and FIG. 13C provides a cross-sectional view.

FIG. 19 is an elevation view of the pivot members and sample plate illustrated in FIG. 18.

FIG. 19A is an elevation view of the pivot members and sample plate illustrated in FIG. 19.

DETAILED DISCUSSION OF THE INVENTION

Figure 1:
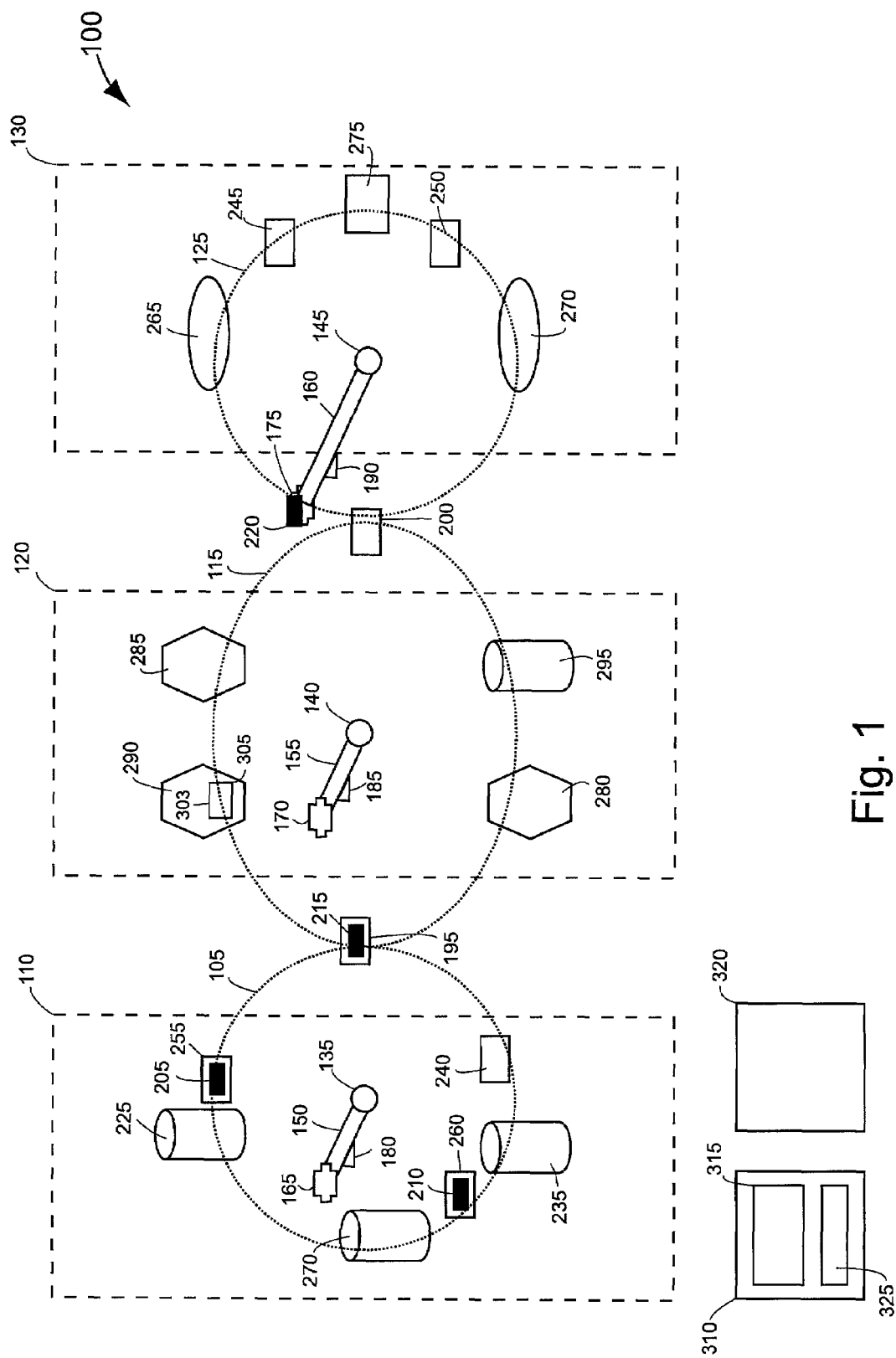
FIG. 1 is a diagram of one example of a high throughput screening system made in accordance with the present invention.

The present invention provides flexible, robust, accurate, and reliable systems and methods for high throughput processing, e.g., for screening large numbers of samples. The present invention alleviates to a great extent the disadvantages of known systems and methods for screening, analysis, and assembly. For example, the present system provides multi-directional and non-linear transport between multiple devices. Accordingly, the present invention improves the reliability, efficiency, and flexibility of processes such as high throughput screening and other methods requiring repetitive manipulations of many individual elements. In addition, the present invention also provides accurate and quick assembly of multi-element devices such as medical devices, testing devices, and/or electronic devices.

A typical system of the invention comprises a plurality of rotational robots, each of which is associated with a work perimeter. Within each work perimeter are a number of devices, e.g., in various station locations within the work perimeter. In addition, each station location and/or device is configured to be accessible by the robot associated with the work perimeter in which the device is positioned. Typically, at least one work perimeter has at least two devices that are exclusively within the reach of the associated rotational robot.

Transfer stations are also typically included, e.g., between work perimeters, to facilitate transfer of samples from one work perimeter to another work perimeter. Furthermore, the whole system is typically coupled to a controller, e.g., a PC, e.g., for directing transport of sample holders between devices and directing processing by those devices. The controllers are typically configured to receive operator instructions and provide operator information.

The systems of the present invention provide flexibility in multiple ways. For example, the devices used in the systems of the invention are optionally arranged and positioned at selected station locations according to the specific requirements of a desired application. Therefore, the entire system is optionally tailored to a specific application. In addition, the systems offer flexibility within each application. For example, the devices in the system are optionally accessed in any order. The controller is optionally programmed to access the station locations in any order, including backtracking to a previously used assaying device. The random access and random processing provided by the present system increase throughput and provide a system that is not limited by the speed of the robot.

Advantageously, each robot efficiently effects the transfer of objects between all devices within that robot's work perimeter. Such close association between each robot and its associated devices facilitates increased throughput, reliability, and accuracy. Further, since devices and/or station locations are easily added, removed, or reconfigured, the systems are highly flexible. Because each work perimeter preferably contains a plurality of station locations and/or devices, the overall system generally requires relatively few work perimeters and associated robots to perform a given automated process. Accordingly, transporting samples from one end of the process to the other end of the process is efficiently and rapidly accomplished. More advantageously, the present invention provides for multi-directional transporting within the system. Processing optionally occurs in any order and is independent of the physical configuration of the station locations. A system made in accordance with the present invention performs high throughput processing quickly, accurately, and with great flexibility, as described in more detail below.

For example, a robot in a first work perimeter is optionally used to transport a sample holder from a storage module, e.g., located in a first work perimeter, to a transfer station, from which transfer station the sample holder is retrieved by a second robot and transported, e.g., to a second work perimeter. Alternatively, aliquots of samples in the sample holder can be transferred at the transfer station to a different sample holder such as, for example, an assay sample holder. In the second work perimeter, the sample holder is optionally processed, e.g., by transporting the sample holder to one or more devices for assaying the sample. The processing steps are also flexible, in that a sample is optionally assayed, detected, and then assayed again, e.g., using a second assaying device or by transporting the sample holder back to the first assay device. The samples are therefore optionally allowed to proceed, e.g., from an assaying step, to a dispensing or detecting step, and back to the assaying step, e.g., as directed by a controller, without having to rearrange the entire system or having an operator manually transport the samples. This flexibility decreases the need for reconfiguration of the system, e.g., by moving various devices around, thereby also decreasing the risk of contamination, e.g., by decreasing the need to handle the sample containers.

The samples processed by the systems of the invention are typically contained in one or more sample holders, e.g., microwell plates, such as 96, 384, or 1536-well plates. Such samples include, but are not limited to, genetic material, such as cDNA, chemicals, biochemicals, serum, cells, cell extracts, nucleic acids, proteins, enzymes, antibodies, carbohydrates, lipids, blood, inorganic materials, and the like.

The systems of the present invention are optionally used for high throughput screening of samples, e.g., of chemical compounds against, for example, cells, cell extracts, and/or particular molecular targets. Accordingly, the invention enables the identification of novel, bioactive compounds that modulate biological processes and the identification of cellular and molecular targets, e.g., of small molecules.

Chemical compounds identified by high throughput screening are optionally used as tools for probing and profiling cell responses and the key molecular entities underlying them. In addition, chemical compounds identified using the present invention are optionally used as lead compounds for therapeutic, prognostic and diagnostic applications. As one example, the present invention performs efficient, comprehensive, functional pathway scans on intact cells, thereby screening, e.g., about 100,000 putative perturbagens per day in a 1536-well format. More preferably the cell-based, biochemical, or other screening systems of the invention screen about 350,000 samples in about 1 to about 4 days with high reliability, and most preferably, about 700,000 samples in about a day (24 hours). The large capacity ultra high throughput system also provides reduced costs, e.g., on a per assay basis.

In another embodiment, the present invention enables high throughput screening of cDNA oligonucleotides against cells and sub-cellular targets, e.g., to identify specific molecular targets associated with particular biochemical pathways. Accordingly, the present invention permits comprehensive and sensitive functional profiling of the entire genome of a particular organism.

In another embodiment, the present invention encompasses functional screening of antibodies to intracellular targets; purified affinity-selected 2-hybrid hits; peptides; and both wild-type and mutant proteins.

In summary, the present invention provides a high throughput processing system that is not limited by robot speed or rectilinear sequential access to devices. The present system provides random access to and multidirectional transport between multiple devices. In addition, the system provides reliable and accurate processing, e.g., for large numbers of samples, e.g., in an ultra-high throughput manner, e.g., using 1536-well plates. Each component of the system is discussed in detail below, followed by example systems and methods of using them.

I. A High Throughput Processing System

The present invention provides high throughput processing systems that are useful, for example, for screening large amounts of target molecules. The systems typically provide an automated robotic process for handling, mixing, moving, storing, assaying, and detecting samples. For example, the systems are optionally designed to carry our assaying, measuring, dispensing, and detecting steps, e.g., on a plurality of multiwell plates.

Typically, the systems comprise a plurality of work perimeters and a plurality of rotational robots, e.g., about 2 to about 10 robots. Each rotational robot is typically associated with one or more member of the plurality of work perimeters. For example, the robots each have a reach which reach defines the work perimeter associated with that robot. The plurality of work perimeters and the plurality of rotational robots are configured to allow transport one or more sample holder along a multi-directional path, e.g., to provide a flexible transport system for a plurality of sample holders. In addition, the systems comprise at least one device associated with each work perimeter. Typically, at least one of the work perimeters has two or more devices exclusively within the reach of the associated rotational robot for that work perimeter. The system is configured to provide non-sequential transport between the two or more devices, with each device being accessible by at least one of the rotational robots. To further aid the transport of the plurality of sample holders, the systems typically comprise one or more transfer station associated with at least a first work perimeter and a second work perimeter. The transfer stations provide transportation of samples (either by transferring the holders themselves or by transferring aliquots of samples from one sample holder to another) between work perimeters, e.g., from the first work perimeter to the second work perimeter. Each of these elements is described in more detail below.

A. Rotational Robots

The systems of the invention are typically based around a plurality of rotational robots. For example, a system of the invention typically comprises about 2 to about 10 rotational robots. Preferably, the robots each have a rotational range of close to about 360 degrees, e.g., they rotate about a rotational axis a full 360 degrees or almost a full 360 degrees. In addition, each robot typically adjusts vertically and horizontally to align with relatively higher or lower work positions.

Preferably, each rotational robot has a robotic arm that extends and/or retracts from the robot's rotational axis. Accordingly, each rotational robot has an associated rotational reach, e.g., defining how far out from the base the robot operates. The rotational reach defines a work perimeter, e.g., a circular work perimeter, for that robot.

Further, each robotic arm typically has a robotic gripper. For example, a gripper is used to aid pick up and delivery of sample holders. The grippers are typically configured to removably couple with a specimen plate, such as standard 96, 384 or 1,536 well plates. A single gripper mechanism is optionally configured to accommodate any size plate. Further, the robotic grippers can be configured to handle other styles of sample holders, including without limitation, custom sample holders, reaction vessels, flasks, crucibles, petri dishes, test tube arrays, or vial arrays. The robotic arms and robotic grippers are typically operated pneumatically, magnetically, or by other means known in the art. The grippers typically provide increased reliability, e.g., by use of pneumatic breakaway grippers. For example, a gripper apparatus typically comprises a member, e.g., a deflectable member, structured to couple the gripper apparatus to a robotic member, which member is structured to deflect when the gripper apparatus contacts an item with a force greater than a preset force. For example, see e.g., U.S. Ser. No. 09/793,254, entitled "Gripper Mechanism," filed Feb. 26, 2001.

In some embodiments, the grippers incorporate optical sensors, e.g., for detecting which sample holders are being transported and which direction a particular sample plate should be inserted into a device, e.g., a plate reader. In addition, a sensor optionally determines a location of the gripper apparatus relative to the object to be transported.

In one embodiment, three Staubli RX-60 robots are used. The robots are typically pedestal mounted robots, e.g., attached to the floor or other surface. Stäubli RX-60 robots are commercially available from Stäubli Corporation, 201 Parkway West, P.O. Box 189, Hillside Park, USA-Duncan, S.C. 29334 (USA). Such robots are highly accurate and precise to within about one one-thousandth of an inch. However, any other type of rotational robot is also optionally used in the robotic system.

Figure 15:
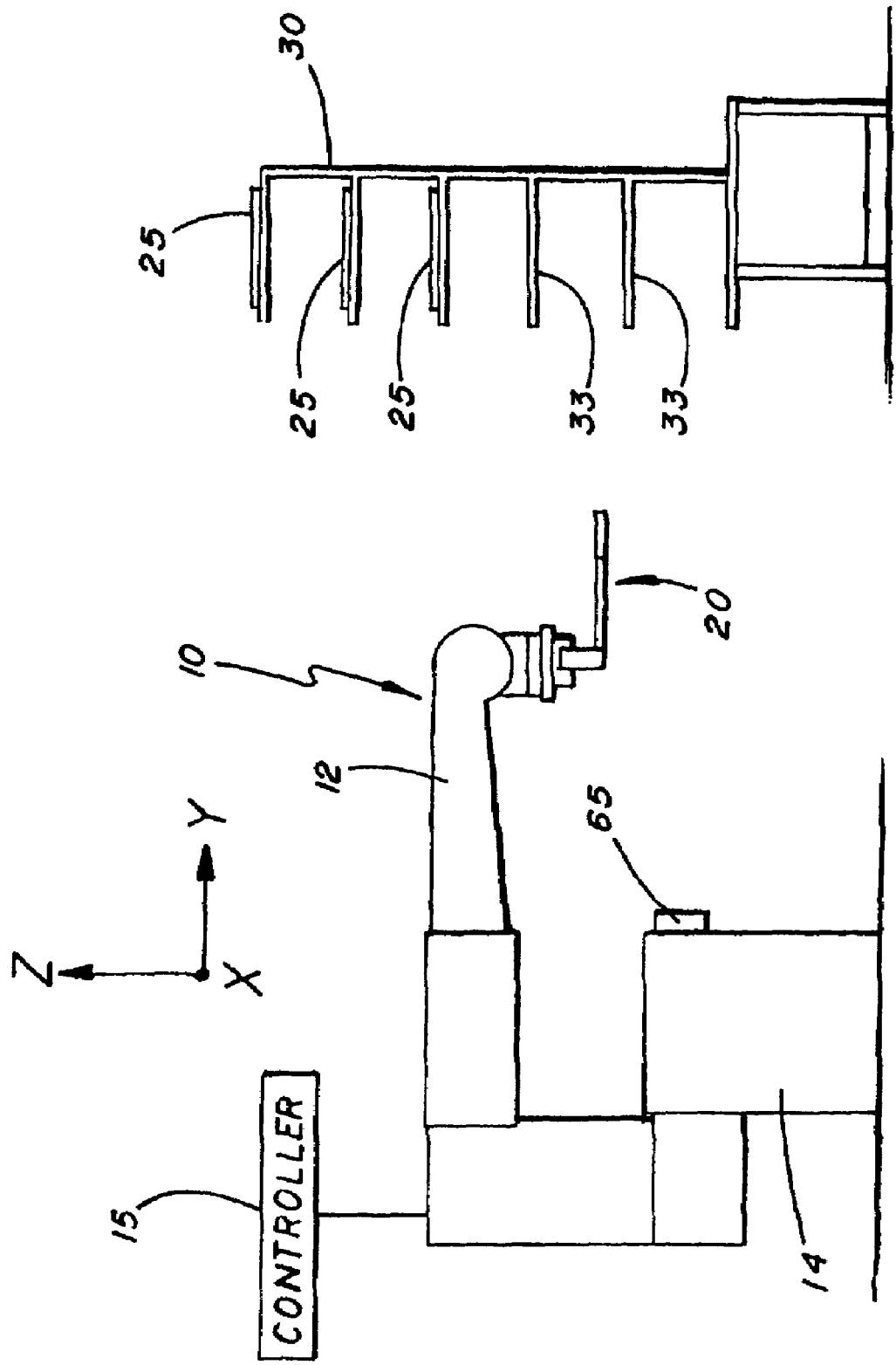
FIG. 15 is an elevation view of a robotic arm gripper mechanism constructed according to one embodiment of the present invention.

Referring to FIG. 15, the robotic gripper mechanism in accordance with one embodiment of the invention is illustrated and designated generally by the numeral 10. The robotic gripper mechanism 10 is an automated and robotic gripper for grasping, moving and positioning objects. The preferred embodiment is constructed to grasp sample plates, but other types of objects can be grasped by the robotic gripper mechanism 10. For example, petri dishes, test tubes, vials, crucibles, reaction vessels or flasks, or any type of object that is employed in a process requiring accurate positioning.

In the prefeffed embodiment illustrated in FIG. 15, the robotic gripper 10 comprises a grasping mechanism 20 movably connected to a boom 12 that is movable relative to a base 14. Controller 15, comprising a general purpose computing device, controls the movements of the grasping mechanism 20 and the boom 12 in a work perimeter that includes one or more stations 30 that can receive sample plates 25. The grasping mechanism 20 is designed to grasp the sample plates 25 and move them from one station 30 to another station 30 or to other locations within the work perimeter of the robotic gripper mechanism 10. Although the disclosed example has one work perimeter, more work perimeters, each employing a robotic gripper mechanism 10, may be utilized, depending upon the specific application.

Refeffing again to FIG. 15, the boom 12 is capable of about 360 degrees of rotation. In addition, the boom 12 can move vertically and horizontally to align the grasping mechanism 20 with higher or lower stations 30.

The boom 12 is configured to extend and retract from the base 14. This defines the work perimeter for the robotic gripper mechanism 10. Stations 30 are positioned within the work perimeter of the boom 12 as are hand-off areas or other areas that are configured for receiving objects grasped and moved by the grasping mechanism 20. For example, sample plate 25 is positioned on station shelf 33 and can be grasped by grasping mechanism 20 and moved to another position by boom 12. In a preferred embodiment, the sample plate 25 comprises several individual wells, with each well configured to hold a sample. For example, a sample plate 25 may contain 384, 967, or 1,536 wells. The grasping mechanism 20 can grasp many other types of sample plates. Other types of devices, such as semiconductor wafers, CDs, medical devices and other items, may be grasped and moved by the grasping mechanism 20.

Figure 16:
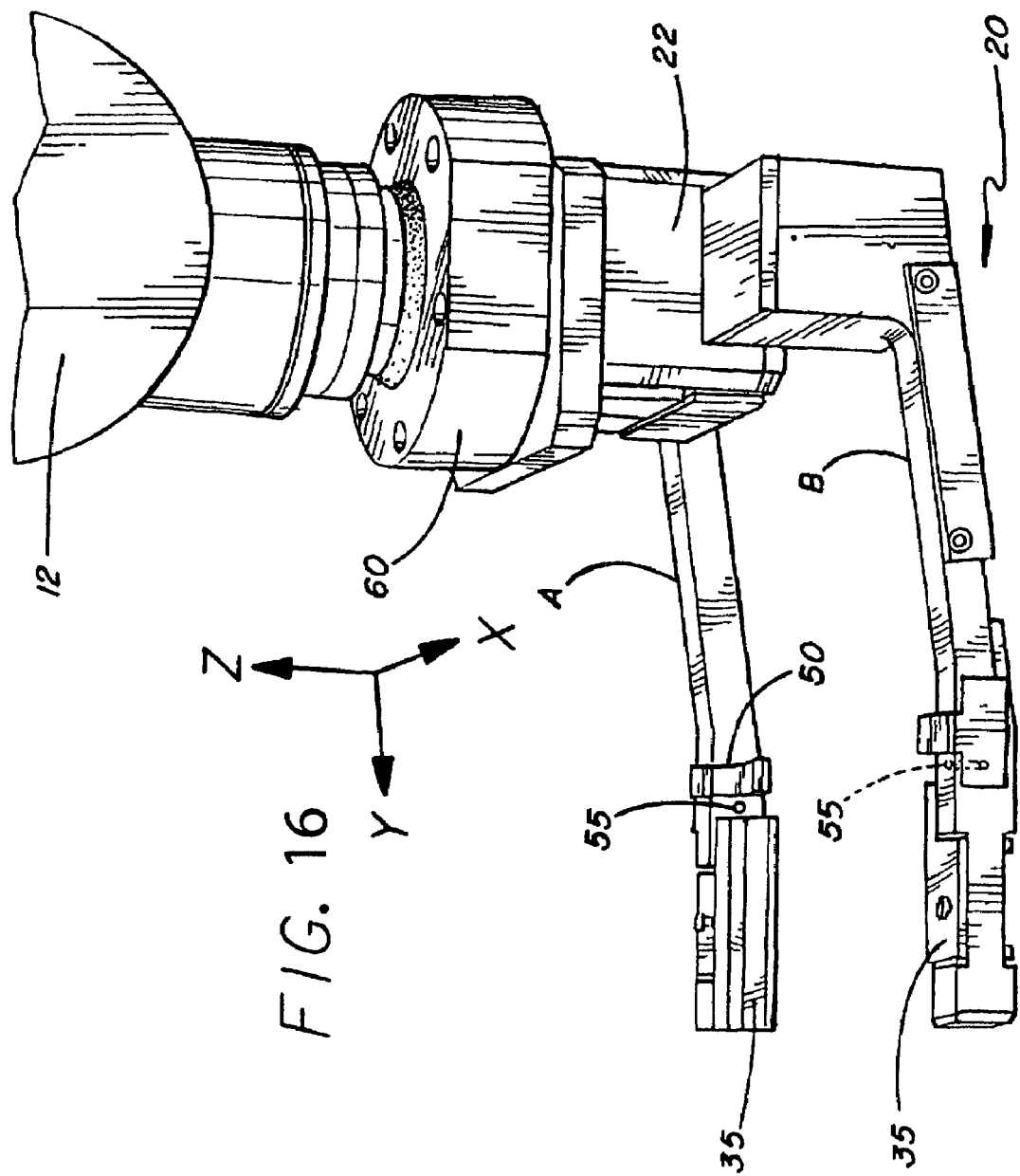
FIG. 16 is a perspective view of the gripper mechanism illustrated in FIG. 15.

Refeffing to FIG. 16, grasping arms A and B extend from the body 22 and include pivot members 35. Positioned adjacent to the pivot members 35 are sensors 55 and stops 50. The sensors 55 communicate with the controller 15 and determine the location of objects adjacent to the arms A and B. In a preferred embodiment, the sensors 55 are optical sensors, but photoelectric, infrared, magnetic, or other suitable sensors can be employed.

Figure 17:
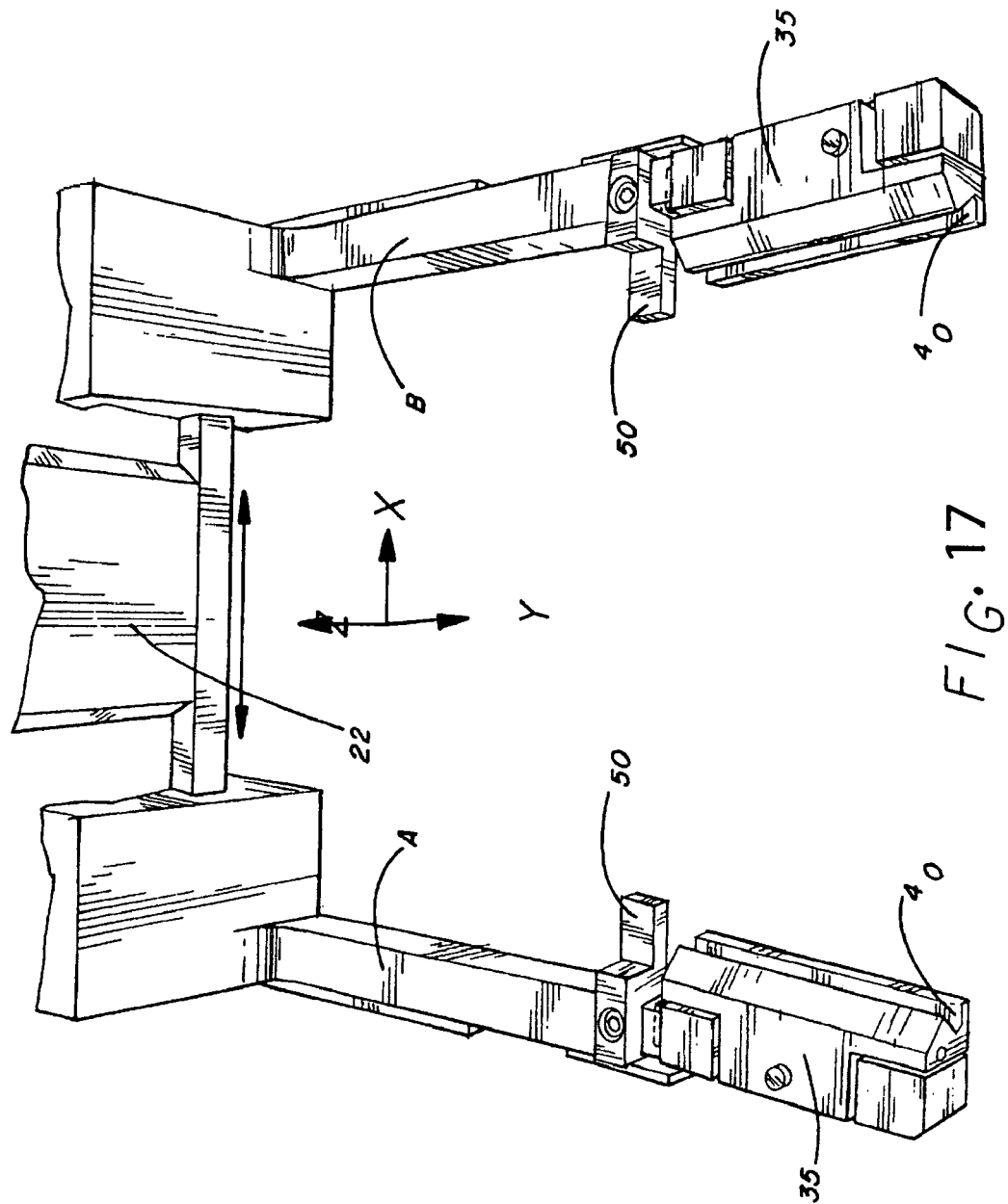
FIG. 17 is a plan view of the gripper mechanism illustrated in FIG. 16.

Refeffing to FIGS. 17 and 19-19A, the pivoting members 35 are pivotally mounted to the arms A and B. A channel 37 extends along a long axis of each pivot member 35 and, as shown in FIG. 19, includes a horizontal surface 40 and an angled surface 45. In a preferred embodiment, the pivot members 35 comprise separate pieces which are pivotally mounted to the arms A and B. An alternative embodiment robotic gripper mechanism 10 may employ grasping arms A and B that include channels 37 in the arms A and B. The arms A and B would pivot with respect to the body 22, thereby eliminating the need for separate pivot members 35. The grasping arms A and B and pivot members 35 preferably are constructed from a metal or alloy, such as aluminum, but dielectric materials, such as plastic or other types of materials, can be employed.

Figure 18:
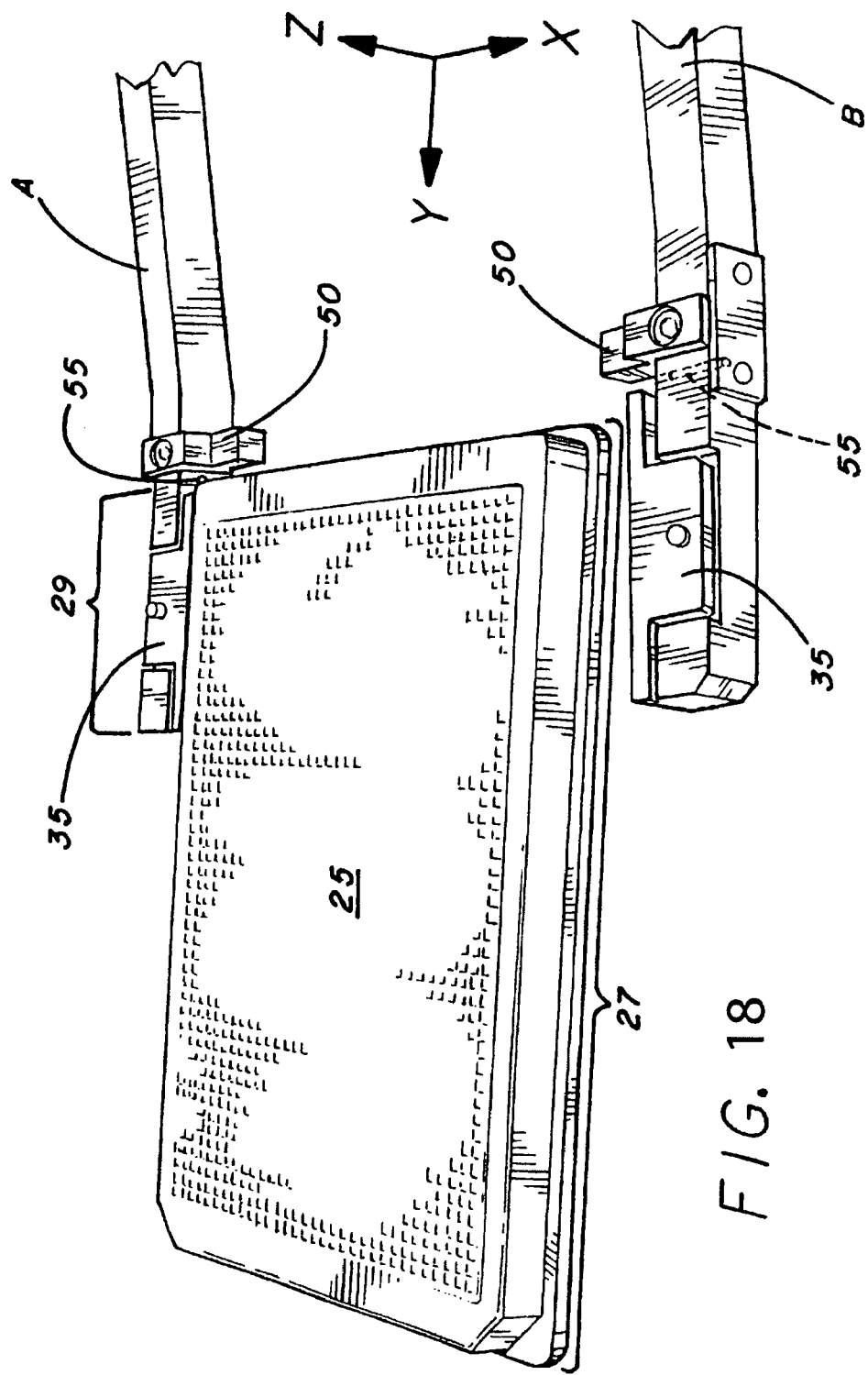
FIG. 18 is a perspective view of the gripper mechanism and sample plate illustrated in FIGS. 15 and 16.

As shown in FIG. 18, the sample plate 25 comprises a plurality of closely arranged sample wells. Each well in the sample plate 25 is square with each side of the well having a length of about 2 millimeters. During a high throughput process, discrete fluid samples may be deposited in each well, requiring positioning accuracy to within 0.1 millimeters. The robotic grasping mechanism 10 of the present invention is capable of this positioning accuracy.

Refefing to FIGS. 19 and 19A, the pivot members 35 comprise a substantially horizontal surface 40 and an angle surface 45 that combine to form a channel 37. As the pivot members 35 approach the sample plate 25, the vertical position of the sample plates 25, defined by the z-axes, may not cofrespond with the pivot members 35. In this case, when the pivot member 35 engages the sample plate edge 27, the edge 27 may contact the angled surface 45. As the grasping arms A and B continue to compress together, the grasping arms A and B pivot slightly, pushing the sample plate 25 against the horizontal surface 40. By including the angled surface 45 on the pivot members 35, the vertical position, as defined by the z-axis, is always known because the angled surface 45 forces the sample plate 25 to engage the horizontal surface 40. This is in contrast to conventional gripping devices that do not define the vertical position of the grasped object. In addition, with conventional grasping devices, an object that is misaligned relative to the x-axes, that is, angled relative to the conventional grasping device, will be grasped at an angle, thereby only establishing a single point of contact on each side of the object.

The robots and associated work perimeters and station locations are typically attached to one or more frames that support the system. For example, weldments or aluminum extrusion are optionally used to provide support frames, e.g., with optical table tops for mounting various devices, e.g., detectors and the like. Such table tops are typically commercially available, e.g., from Melles Griot (Irvine Calif.).

The robots of the system are typically used to transport one or more sample holder. For example, the robots transfer samples, e.g., in sample holders, from one work perimeter to another work perimeter, e.g., via a transfer station. To transfer between adjacent work perimeters, a first robot retrieves a sample holder or plate, positions the plate at a transfer station, and then a robot from an adjacent work perimeter retrieves the plate from the transfer station. Alternately, the robots are configured to directly transfer a sample plate from one robot to a second robot. Preferably, the robots transfer sample holders from device to device or work perimeter to work perimeter in about 1 to about 10 minutes, more preferably in about 1 to about 5 minutes.

In addition, the robots transfer sample holders between station locations within the associated work perimeter of the robot at issue or between devices. In this manner, the sample holders are transported to the devices of the invention, e.g., for further processing, measurement, or detection.

Because the robots are rotational, i.e., they rotate about an axis, and are positioned or configured to access an entire work perimeter, the devices or station locations within the work perimeter are randomly accessed, e.g., no particular order must be followed when transporting sample holders to and from the devices. The robots therefore, provide multidirectional and/or non-linear transport within the system, allowing sample holders to be brought directly to the desired station or device without traversing an entire preset path. This increases the throughput of the system to beyond that of presently available systems.

B. Work Perimeters

A "work perimeter," as referred to herein, is an area within the rotational reach of a robot. The work perimeters of the present invention typically comprise one or more station location, and preferably two or more station locations. The station locations are used to perform various processes, assays, and the like, e.g., on the samples within a sample plate or holder. Typically, the work perimeters are defined by the rotational reach of a rotational robot as described above. For example, FIG. 1 comprises three work perimeters: area 105, 115, and 125. The work perimeters comprise the area in which devices and stations are placed and are defined by the rotational reach of the robots 135, 140, and 145. The rotational reach areas are shown as circles or ovals but are optionally any other shape, depending on the reach and extension of the robot arm. Typically, at least work perimeter has two or more devices exclusively within the reach of the rotational robot within that work perimeter. In some embodiments, two or more work perimeters have two or more devices exclusively within the reach of the rotational robot within each particular work perimeter. In the specific embodiment shown in FIG. 1, all three work perimeters each have two or more devices exclusively within the reach of the respective robot. The high throughput processing systems of the invention, in some embodiments, have three or more devices exclusively within the reach of the rotational robot within that work perimeter.

Although FIG. 1 illustrates three work perimeters, the number of work perimeters is optionally less than or more than three, depending on specific assay requirements. Typically a work perimeter is provided for each rotational robot in use and the work perimeter extends at least as far as the rotational reach of the robot. The devices associated with each work perimeter can encompass additional space, for example, as shown as 110, 120 and 130 in FIG. 1. The rotational robot need reach only far enough to place a sample or sample holder in or on the desired device. For example, a dispensing device optionally uses up space beyond the rotational reach of an associated robot, e.g., to accommodate a pump and or a waste receptacle, yet the robot optionally reaches only far enough for the dispensing device to receive the sample holder.

Each work perimeter is optionally directed to a certain task or group of tasks, e.g., using the station locations and devices located within that area. For example, a first work perimeter is optionally used for storing samples or compounds, while a second work perimeter is used for processing a sample or group of samples, e.g., by adding reagents, shaking, heating, incubating, or the like. A third work perimeter is optionally used for analyzing and/or detecting the samples once they have been assayed. For example, a sample is optionally separated into various components, which are then detected, e.g., using a fluorescent detector. Alternatively, each work perimeter is directed to a particular type of assay in a process that involves multiple assays. Although each work perimeter is generally directed to a particular type of task, e.g., detection, storage, or the like, the functionality of the work perimeters is optionally overlapping. For example, a work perimeter that is generally used for storage, may also be used to perform a heating step in an assay of interest or some other processing step.

One advantage of the present invention is that there is no particular order that must be followed in transporting samples between work perimeters, as is the case in many of the existing systems. Because the system has multidirectional utility, samples are optionally transported from the first work perimeter to the second work perimeter and then back to the first area, e.g., for further processing, prior to detection in a third work perimeter. This provides an operator the ability to respond, e.g., to results or information gathered in a first assay, and reprogram the system accordingly for further processing, e.g., further dilution in a different work perimeter can be directed during operation if a sample is found to be too concentrated in a detection step.

Furthermore, because each work perimeter preferably accommodates a plurality of devices, and work perimeters are positioned adjacent each other, an entire high throughput screening system is optionally configured to fit into a reasonably compact physical space. For example, a system as shown in FIG. 1 can fit in an 18'×12' space. Fitting into a compact space not only is efficient from a cost standpoint, but also facilitates efficient movement of sample holders between work perimeters and from one end of the system to the other end of the system. By enabling a compact physical arrangement, the speed and efficiency of the overall system are increased. Further, because peripheral devices are compacted into a small physical area, the amount of time a specimen plate is in transport, and potentially uncovered, is reduced. Thus, the risks of contamination and undesirable evaporative effects are reduced. Another advantage of the compactness of the present invention stems from the ability to enclose the entire system into a chamber with a well-controlled environment. As such, environmental effects such as temperature, pressure, humidity, and particle content can be strictly maintained.

Each work perimeter typically comprises one or more devices, e.g., as described below. At least one work perimeter typically has at least two devices within it that are exclusively within the reach of the associated robot. Example devices compatible with the present systems are provided below.

C. Devices

Typically, each work perimeter in the high throughput systems of the invention contains a plurality of devices. These devices can be, for example, automated instruments. Automated instrument devices are used, e.g., to store, process, and/or detect samples, e.g., in sample holders. For example, devices are provided in the work perimeters for storing, assaying, dispensing, and measuring fluids, reagents, samples, and the like.

The devices are typically located in or on a station location, e.g., a platform or table comprising electrical connections and computer and/or controller connections. The devices are typically positioned at a station location prior to operation of the system, however, a device is optionally added to a station location during operation of the system as well. In addition, the devices are optionally moved around within a work perimeter, e.g., either before operation of the device or upon reconfiguration prior to using the device for another application. The devices need only being positioned within a work perimeter, e.g., to be within the reach of the rotational robot associated with the work perimeter. If enough station locations are not available, a device is optionally positioned within the reach of the robot without a dedicated station location. Typically at least two devices within at least one work perimeter are exclusively within the reach of the associated robot.

Typically each station location in the system contains a single device, however, multiple devices are optionally positioned at a single location as well. In addition, the system may comprise station locations that do not have associated devices or devices that are not associated with a station location. Unoccupied station locations are optionally used for storage, temporary holding of sample holders, or simply not accessed during operation of the system. In addition, all devices are not necessarily used during operation of the system. A number of devices are typically positioned within the station locations of the system prior to operation. During operation of the system, all of the devices are optionally used or only a portion of the devices may be used. Because the rotational robots access each station location independently, the devices are accessed in any order desired, including skipping some devices all together and/or repeatedly accessing one or two devices. An operator typically programs the system, e g., via a controller, to transport the sample holders from device to device as desired for a particular application.

In addition, the devices typically each have a receiving module, e.g., for receiving a sample holder. In some cases, the receiving module couples to a gripper or positioning device on a robotic arm. In some devices, the sample holder is placed on a conveyor by the robotic arm or placed in a sample compartment. For example, the robotic arm optionally opens a door on an incubator and places the sample holder inside the incubator, e.g., in a plate carousel.

The devices used in the systems of the invention include, but are not limited to, compound storage devices or modules, liquid dispensers, workstations, replating stations, thermocyclers, incubators, heating units, pumps, detectors, electrophoresis and/or chromatography modules, purification and/or filtration modules, wash modules, centrifuges, PCR modules, vacuums, refrigeration units, mixing plates, weighing modules, light sources, and other types of devices known to those of skill in the art. Such devices are used to perform a variety of techniques including, but not limited to, PCR, hybridizations, cloning, translation, transcription, isolations, cell growth, washes, dilutions, detection, and the like. Some typical devices are described in more detail below.

Compound storage devices, such as, specimen plate hotels, nests, and the like, are optionally included in one or more work perimeters, e.g., at a station location. For example, an operator optionally uses one or more plate hotels to introduce a set of sample holders into the system. For example, an operator optionally retrieves a set of plates from a long-term storage area, e.g., not connected to the system; places the plates in a hotel; and registers the plates with the system, e.g., for inventory purposes. The operator then typically specifies that the newly introduced plates should be processed by the system. Alternatively, a storage system, e.g., a long term storage system, is optionally coupled, e.g., via a conveyor or rotational robot, to a high throughput system, e.g., for storage and automatic retrieval and entry into the system.

When multiple storage modules are used in the system, they are optionally identical devices such as those that are commercially available, or devices specifically configured for a particular application. For example, compound storage devices are optionally refrigerated, dehumidified, or maintained under an inert atmosphere for storing particular types of chemical, genetic, viral, or cellular material. Other storage devices are optionally configured to be at substantially room temperature, or to be warmed, e.g., to 37 degrees centigrade.

The storage compartments in the present invention typically have a storage capacity of least about 350,000 samples, at least about 700,000, or at least about 1,400,000 samples or more. In addition, other systems and devices are optionally used for storing and retaining samples, e.g., temporarily or for extended storage.

In one embodiment, an incubator or storage compartment of the invention optionally comprises a housing, which housing has a plurality of doors. Example storage devices are illustrated by storage device 235 in FIG. 1. For example, storage device 235 optionally includes two 522 plate capacity carousels, dry nitrogen for cooling, and "VCR doors" for access. The doors close at least one opening disposed through at least one surface of the housing. In addition, the housing includes at least one movable shelf disposed therein, which shelf is capable of aligning with the opening. Each of the plurality of doors is independently accessible, e.g., by a rotational robot of the system. See, e.g., U.S. Ser. No. 60/306,481, filed Jul. 18, 2001.

Other devices which are optionally placed in or positioned on station locations in the present systems include, but are not limited to, devices for dispensing or transferring liquids or other reagents, e.g., pin tools, syringes, pumps, and the like. In addition, a low volume liquid dispensing system is optionally used in the present systems, e.g., to increase reliability of the system.

In high throughput systems, small volumes of liquid are often used and a need exists to dispense them accurately, e.g., into wells, with as little waste as possible, to provide a reliable system. Such dispensing devices are described, e.g., in U.S. Ser. No. 09/562,652, entitled "Method and Apparatus for Dispensing Low Nanoliter Volumes of a Liquid While Minimizing Waste", filed May 2, 2000; and in U.S. Ser. No. 09/818,748, entitled "Apparatus and Method for Preparing Fluid Mixtures," filed Mar. 27, 2001; which are herein incorporated by reference as if set forth in their entirety.

In one embodiment, a fluid transfer device of the invention aspirates a volume of sample into one or more of receptacle from one or more wells of a multiwell plate which is aligned with the outlet of the receptacle. A substantial portion of the volume of the aspirated sample is returned to the well of the multiwell plate, in which the returned volume of the liquid is less than the aspirated volume so that a volume of sample is retained in the receptacle. A portion of the retained volume of sample is dispensed, e.g., into a well of a second multiwell plate, with any remaining volume of the retained liquid typically being discarded. See, e.g., U.S. Ser. No. 09/562,652, for more information. Typically, the volume of the aspirated sample is at least several times the volume of the dispensed sample.

In other embodiments, pin tools are used for dispensing fluids, e.g., reagents, simultaneously into multiple sample wells. Pin tools are commercially available, e.g., from V & P Scientific, Inc., San Diego, Calif. For example, an array of pin tools that aligns with a plurality of wells in a microwell plate is optionally used to transfer an aliquot of a sample from wells of one multiwell plate to wells of another multiwell plate.

Devices comprising pin tools device also optionally include one or more wash stations in which the pins are washed between transfers. For example, after transferring a fluid from one multiwell plate to another, the pins are optionally washed before using them for addition of a second reagent, e.g., a different dye solution, or a different transfer. The present invention also provides methods of washing a pin array. The methods typically comprise sequentially dipping an array of pins into a series of wash solutions, such as DMSO, alcohol, water, and the like.

Other fluid dispensing devices are also optionally used in the present invention. For example, at least one sample holder or assay holder is optionally a multiwell plate with which a fluid transfer device aligns. The fluid transfer device in this case typically comprises an array of receptacles arranged such that the outlets of the receptacles are aligned with a plurality of wells on the microwell plate, e.g., a 96-well or 384-well plate. The Robbins Hydra is one example of such a dispensing device. The Robbins Hydra 384 or 96 (Robbins, Scientific, Sunnyvale, Calif.) peripheral device is an integrated workstation that includes, e.g., 100 microliter syringes. The syringe tips are typically made of the titanium alloy Duraflex. This peripheral device provides custom dispensing, e.g., of 50 nanoliter volume samples. Dispensation of such small volumes is particularly desirable for applications such as, for example, high throughput protein crystallography.

Other fluid manipulation devices optionally used in conjunction with the present systems include those dispensing systems that incorporate positive displacement pumps and dispenser valves, e.g., coupled to the pumps. For example, a Cartesian SynQUAD (available from Cartesian Technologies, Inc., Irvine, Calif. and described in U.S. Pat. No: 6,063, 339) provides an integrated workstation that dispenses bulk amounts of material, e.g., about 0.5 to 5.0 microliters of fluid per well of cells or reagents, at the rate of about one to about two minutes per plate. The SynQUAD comprises many components that are optionally positioned on a lab bench or a station location of the present invention. Pumps typically connect each component to a main module and to a computer, e.g., with about 80 connections. Software is optionally installed, e.g., on a supervisor PC, to direct and control each component. Therefore, the system is readily adaptable for use in the systems of the invention.

A multi-drop peripheral device is also optionally placed on a bench for installation of tubing, e.g., with a preassembled cassette, for dispensing of material. This device is also compatible with the robotic system of the present invention.

Typically, the fluid dispensing and transfer devices of the invention do not comprise disposable pipette tips. In one embodiment, the entire system contains no disposable pipette tips.

Incubator devices are also optionally used in the systems of the present invention. For example, an incubator device is optionally positioned in a station location within a work perimeter, e.g., work area 110 and station location 380 in FIG. 3. The incubator is optionally set to provide a desired temperature, humidity, oxygen, $N_2$, or $CO_2$ level, e.g., for facilitating growth of cellular material. Due to a particular environment within the incubator, the incubator optionally comprises a sealed door, provided, for example, by an airlock. Accordingly, a sealed door preferably has a gripping structure, which gripping structure is typically configured for coupling to a robotic gripper on the robotic arm of a robot, e.g., in the same work perimeter. In such a manner, the robotic arm positions the robotic gripper adjacent to the gripping structure and opens and closes the door. As the robot opens and closes the door, a temporary holding area positioned adjacent to the incubator is typically used for temporarily holding a sample holder, e.g., as it is moved into or out of incubator. In addition, an incubator device of the invention optionally includes custom VCR doors and one or more plate carousel. An example incubation system for use in the present invention is described, e.g., in U.S. Ser. No. 60/306,481, entitled "High Throughput Incubation Devices (VCR DOORS)," filed Jul. 18, 2001.

Detectors are also typically included in at least one work perimeter of the invention. These devices are optionally any detection device or any device used to measure physical properties of a sample. For example, fluorescence, luminescence, phosphorescence, x-ray, radio-frequency (RF), electrical or optical detection, such as IR or UV, electrochemical detection, enzymatic or binding assays, radioactivity, nuclear magnetic resonance spectrometry, light scattering, chromatography, or mass spectrometry, e.g., electrospray MS, are optionally used to quantify and/or characterize various properties of the sample. Alternatively, the detection devices are charged-couple devices (CCD) or bottom scanning devices. In one embodiment, a camera is used to take images of assay results, in which case, the assay results are optionally analyzed at a later point in time. This speeds up the processing throughput because each individual well need not be scanned in real time. Typically, the camera images are stored in a digital format. Other detectors, diagnostic tools, or screening devices known to those of skill in the art are also optionally used to detect, screen, analyze, or otherwise process samples in the present systems.

For example, in cell analysis systems, a variety of detectors are optionally used, such as a Fluorometric Imaging Plate Reader system (FLIPR®), e.g., from Molecular Devices Corp., Sunnyvale, Calif. In addition, Chemiluminescent imaging plate reader is also optionally used (CLIPR™) (Molecular Devices Corp.). It integrates a high sensitivity CCD camera, telecentric lens, high precision positioning mechanism, and computer system with software to control the instrument and record data. In fact, Molecular Devices makes a whole line of microplate reader systems, including luminescence microplate readers, fluorescence microplate readers, absorbance microplate readers that are optionally incorporated into the systems provided herein. For more on imaging systems, e.g., high content imaging, see, e.g., WO 00/17643 (PCT US99/21561).

An LJL Acquest (Molecular Devices, Sunnyvale, Calif.) peripheral device is another integrated workstation optionally used in the present system. It has a multi-mode reader and a modified nest for robotic access.

Other devices, include, but are not limited to, a Modified Forma Incubator, Custom Compound Storage Carousels.

Another automated device of for use in the present systems is a replating system. The device or system is used, e.g., to replate a plurality of samples from one or more small sample plates into a single large sample plate. Because the integrity of a compound collection, e.g., one or more large libraries, and database is of great importance to most discovery processes, management of the compounds is an important issue. Therefore, the present invention also provides a replating system and method for making the difficult transformation from low density format microtiter plates to high density microtiter plates. For example, compounds are optionally transferred or replated from 96 well to 384 well microtiter plates and/or from 384 to 1536 well plates. This is typically a difficult transformation because it is labor intensive, there are many steps in which error can be introduced, it is difficult to track the transformation while at the same time being important to rigorously track it. The present invention provides an efficient and flexible method to track the reformatting of microtiter plates. The system uses visual and readable controls to track the reformatting and allows the user to verify that the reformatting was successful. Such a system is optionally included in the systems provided, e.g., at a station location in one or more work perimeter. Alternatively, the replating procedure is performed in combination with a storage module.

Replating typically involves multiple fluid manipulations. For example, a fluid dispenser, e.g., a programmable fluid dispenser, and a pipettor system are optionally used in a replating device, e.g., to transfer the samples contained in a lower well-density plate, e.g., a 96-well plate or 384-well plate, to a plate having more wells, e.g., a 384-plate or 1536-well plate. In addition to transferring the samples in the smaller sample plate to the higher well density sample plate, the device also provides and/or transfers markers or labels to the higher well density sample plate as explained in greater detail below. A Tecan Miniprep (Tecan US, Durham N.C.), which comprises an automatic sample processor, is one example of a device that is suitable for replating operations.

D. Station Locations

Figure 3:
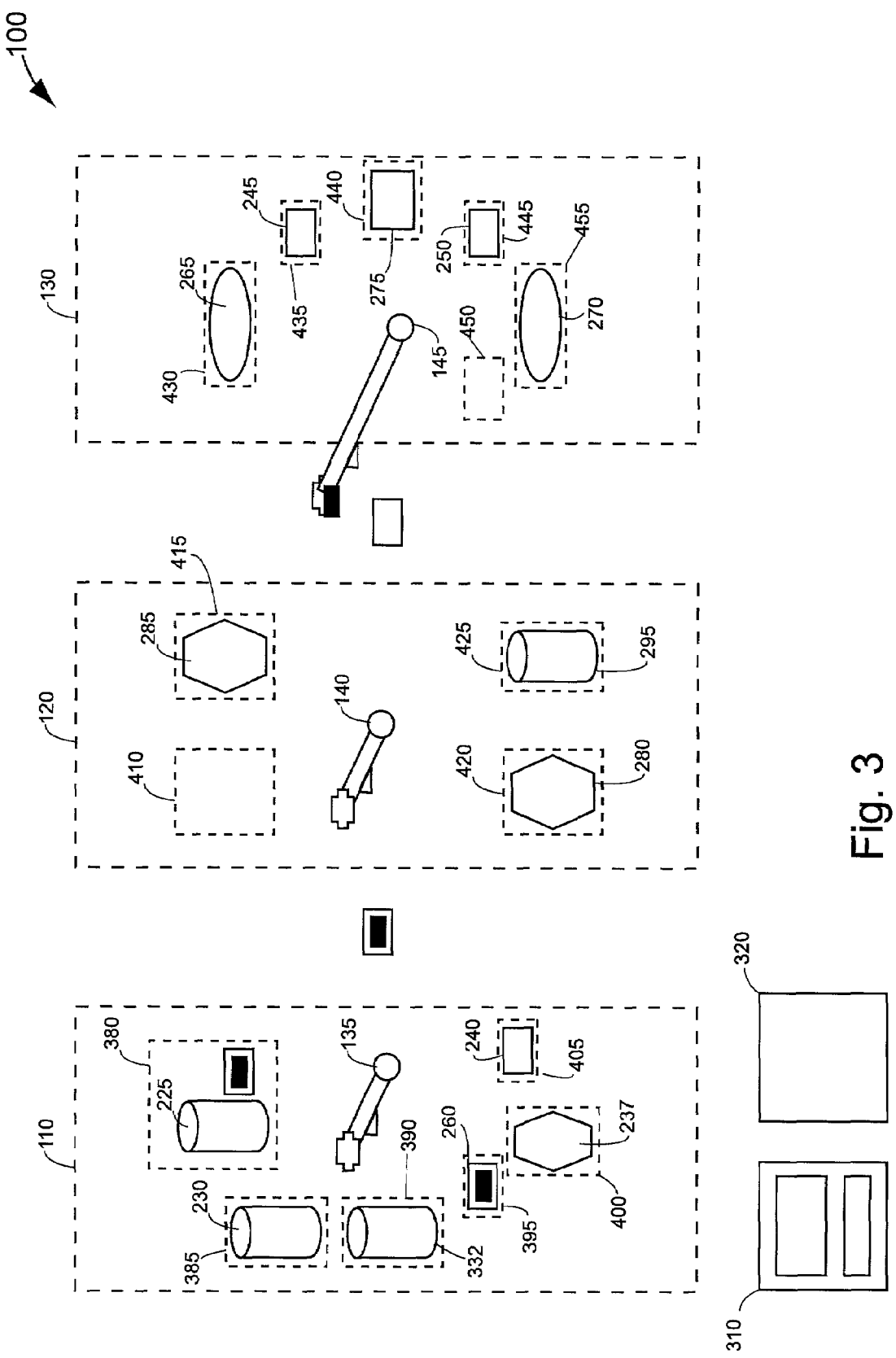
FIG. 3 is a diagram showing station locations for a high throughput screening system as shown in FIG. 1.

A "station location," as referred to herein, is an area within a work perimeter, which area is used to accommodate one or more devices or sample plates. The station location is a place, e.g., a table, platform, or location, which is configured to receive a device, e.g., a fluid dispenser, a plate carousel, a detector, or the like. Each work perimeter of the invention typically comprises two or more station locations. For example, FIG. 3 illustrates various station locations, e.g., station location, 380, 385, 390, 395, 400, and 405, in work area 110. Each work perimeter typically comprises two or more station locations, which station locations optionally comprise one or more device, e.g., an automated device.

Typically, each station location comprises one device for a given assay or process, e.g., a thermocycler, a pump, a fluid dispenser, an incubator, a storage module, or the like. The devices will typically remain at a single station location during an entire process and be accessed, e.g., in any order desired, by the rotational robots.

Alternatively, the station locations are adapted to a particular process before operation of the system, such that every station location comprises a device of use in the immediate process. In this manner, the station locations convey a great deal of flexibility to the system. Each location is typically set up or configured to receive a device. For example, a controller is optionally associated with each station location, e.g., for sending and receiving process information. In addition, electrical connections are typically provided for each station location, such that whenever a new device is desired, the hook up at a station location is easily accomplished. In addition, because the station locations are not necessarily located along a linear path, e.g., a conveyor, the alignment problems are decreased as compared to existing systems.

In some embodiments, however, one or more station locations are empty or unused. For example, a station location optionally is left empty or used as a holding area, as described below. In addition, some station locations have devices positioned therein that are not used in a particular process. In that case, the rotational robots are not instructed to transport the sample holders to that station location. The location is skipped in the transport path selected. No time is wasted by having to transport the sample holders through an unused station. Therefore, the system provides improved throughput and efficiency.

In some embodiments, the station locations comprise platforms, e.g., platforms that are optionally raised and lowered, e.g., mechanically or pneumatically. In other embodiments, the station location is merely a designated place on a table or bench to which a device is optionally affixed. The station locations act as place holders for devices and are optionally any shape and size depending on the devices of interest.

Although high throughput screening system 100, as shown in FIGS. 1 and 3, only defines a select number of station locations, more or fewer station locations are optionally defined depending upon the reach of each robotic arm and the size of selected devices. Further, station locations are optionally added, moved, or removed depending on specific application needs. For example, a given work perimeter optionally includes about 2 to about 10 station locations, more typically about 3 to about 5.

Because station locations can remain the same irrespective of what device is positioned in that station location, the high throughput screening system is easily reconfigured to accommodate a variety of specific needs. Accordingly, high throughput screening systems of the invention are optionally reconfigured to add, delete, or replace devices in any station location. Advantageously, station locations are also optionally added or removed to accommodate changes in the area or robot orientation. Not only is the system thereby flexibly reconfigurable, but the system easily adjusts to accommodate adjustments in work flow.

In addition, to station locations, each work perimeter also optionally comprises holding areas, e.g., temporary holding areas, e.g., for storing sample holders until needed in a particular assay. For example, FIG. 1 illustrates holding areas 245 and 250 in work area 130 and holding areas 255 and 260 in work area 110. Holding areas 255 and 260 in FIG. 1 are shown with sample holders 210 and 205 positioned therein. The holding areas are typically used to temporarily position a sample holder. These holding areas optionally contain nest devices such as static exchange nests or interchange platforms. Other devices that are optionally employed in temporary holding areas are also contemplated within the present invention. In one embodiment, one or more of the static holding areas are used by the operator, e.g., to manually introduce specimen plates into the system. Fewer or more temporary holding area devices are optionally used in the high throughput screening systems of the invention. In fact, the number of holding areas is variable within the same system and is optionally changed from one operation to the next.

In the system illustrated in FIG. 1, holding areas 245, 250, and 260 are positioned away from any instrumentation and provide a temporary resting area, e.g., for a specimen plate. For example, timing considerations sometimes dictate that a specimen plate should rest for a period of time, e.g., at a holding area. In addition, the holding areas are optionally used to carry out one or more processes. For example, filtration of samples, application of vacuum pressure, or UV exposure of the samples in the sample holder, are optionally carried out in a holding area. Also, a holding area optionally accommodates the temporary holding of a sample holder when the next sequential device is not yet available. The robotic system typically retrieves the sample holder from the temporary holding area and moves it to the next sequential device, when available, e.g., after processing is complete.

Typically, the station locations of the invention comprise one or more devices, e.g., as described above, for processing samples, e.g., as described in more detail below.

E. Transfer Stations

A transfer station (or hand-off area) is typically a location located proximal to two or more work perimeters, e.g., for transferring samples or sample holders between work perimeters. In some embodiments, the transfer station comprises one or more platform for placing the sample, e.g., until an adjacent robot retrieves it. However, the transfer station is also optionally an area, e.g., on the system surface or a table surface, in which two or more robotic arms meet and transfer a sample plate directly from one arm to the other, e.g., where adjacent robots directly pass a sample holder from one robot to the adjacent robot.

In addition to transferring samples from one device to a second device or from one work perimeter to another work perimeter, the transfer stations of the invention are also optionally used to transfer samples from one sample holder to another sample holder, e.g., in a replating procedure as described in more detail below. Typically, a sample plate, e.g., containing test compounds for screening, is transferred from a storage module to a transfer station. From the transfer station, samples can be transferred to the adjacent work perimeter. Either the entire sample plate can be transferred to the next work perimeter, or aliquots samples in the sample plate can be transferred to an assay plate. For example, the robot in one work perimeter transfers an assay plate to a transfer station, which transfer station includes a fluid transfer device that takes an aliquot of a test sample (from the sample plate) and puts the aliquot into a well of the assay plate. The plate that contains the test samples is then put back into a storage incubator, and the assay plate is subjected to further processing (e.g., addition of additional reagents, incubation, mixing, etc.). After the desired length of incubation time, the assay plates are moved to a detector. The sample plates and the assay plates never have to leave their respective work perimeters. As used herein, the "test samples" or "test compounds are typically added to assays to determine the effect of the test samples on the assays.

FIG. 1 illustrates two transfer stations. Transfer station 195 is positioned between work perimeter 105 and 115 and transfer station 200 is positioned between work perimeters 115 and 125. In the figure, transfer station 195 comprises sample holder 215, which sample holder is available for pick up by robotic arm 155 or 150. The robotic arms then transfer the plate to any device or station location within the associated work perimeter, e.g., work perimeter 105 or 115.

F. Sample Holders

In the high throughput systems provided, samples are typically stored, processed, and detected using sample holders. A "sample holder" is any container that holds or contains one or more sample, e.g., a dried or fluidic sample. A typical sample holder comprises a multiwell plate, microtitre plate, or specimen plate, which terms are used interchangeably herein. Multiwell plates are typically constructed according to industry standards to have several individual wells, with each well configured to hold a sample. For example, plates typically contain 96, 384, 968, or 1,536 wells. The high throughput systems of the invention are preferably configured to accommodate 96, 384, 968, and/or 1,536 well specimen plates. For example, one work perimeter is optionally configured to accommodate 384-well plates and a second work perimeter configured for 1536-well plates. Alternatively, all work perimeters in a system can be configured for one type of plate (e.g., 384-well plates of 1536-well plates). In addition, many other types of sample holders, for example, custom sample holders, petri dishes, gene chips, assay holders, test tube arrays, vial arrays, crucibles, reaction vessels, or flasks, are also used with the present invention. "Array holders" typically comprise containers in which assay are conducted. For example, an assay holder is also optionally a microwell plate, e.g., one that contains the reagents and/or components for a particular assay or screen. In the present invention, a set of assay holders is optionally used in addition to a set of sample holders. The assay holders typically contain assay components, into which are added test compounds or test samples, e.g., from the sample holders. The test samples are added to the assay holders to determine the effect of the test sample on the assay results.

Samples contained within the sample holders typically include, but are not limited to, biological or microbiological samples, chemical or biochemical samples, cells, cell extracts, serum, plant extracts, parts for an electronic or medical devices, and the like. In some embodiments, the sample holders of the invention optionally contain one or more library of cDNA molecules, library of promoters, or library of gene regulatory regions operably linked to one or more reporter gene. For example, a library of gene regulatory regions is optionally derived from one or more genes that are differentially expressed in a cell, e.g., depending on the presence or absence of a particular stimulus. For assays using these types of libraries, see, e.g., U.S. Ser. No. 60/275,266, entitled "Identification of Cellular Targets for Biologically Active Molecules," filed Mar. 12, 2001; and U.S. Ser. No. 60/275,070, entitled Genomics-Driven High Speed Cellular Assays," filed Mar. 12, 2001. For example, U.S. Ser. No. 60/275,070 describes screens designed to identify gene regulatory regions and methods of producing libraries of gene regulatory regions. U.S. Ser. No. 60/275,266 describes methods for rapidly identifying targets of any molecule that is biologically active. The methods involve making a library of cells in which the level of a molecular target is varied among library members, and identifying those library members that exhibit a change in response to the test compound.

The robotic arms described herein are optionally configured to hold, e.g., for transport, any type of sample container useful for the assays of interest. In addition, the robotic arms typically comprise a gripper mechanism for lifting sample holders. The gripper mechanism is typically configured to hold the various size multiwell plates, e.g., including, but not limited to 1536 well plates. Gripper mechanisms are described, e.g., in U.S. Ser. No. 09/793,254, entitled "Gripper Mechanism," filed Feb. 26, 2001.

To reduce contamination and evaporative effects, it is sometimes desirable to provide at least some of the sample holders with lids. A lid that sufficiently seals a sample holder not only reduces evaporation and contamination, but allows gases to diffuse into sample wells more consistently and reliably. Lids generally have a gripping structure, such as a gripping edge, that the robotic arm gripper engages. Accordingly, a robot is able to lid and delid the specimen plate as needed. Copending U.S. patent application Ser. No. 09/569,325 entitled "Specimen Plate Lid and Method of Using", filed May 11, 2000 discloses a specimen plate lid for robotic use, and is incorporated herein by reference as if set forth in its entirety. In one embodiment, the sample holder lids, e.g., stainless steel lids, comprise a cover having a top surface, a bottom surface, and a side. In addition, an alignment protrusion extends from the side of the cover, e.g., positioned to cooperate with an alignment member of a multiwell plate. The lids further comprise a sealing perimeter positioned on the bottom surface of the cover, wherein the alignment protrusion facilitates aligning the lid to the plate so that a seal is compressibly received between the sealing perimeter and a sealing surface of the multiwell plate. The lids are of sufficient weight to compress the seal and form a tight seal between the lid and the plate. For example, the lids typically weigh between about 100 grams and about 500 grams. A lidding and/or de-lidding station is also optionally included as a device in the present systems, e.g., to add and/or remove the lids described above to or from the sample holders. Alternatively, the entire robotic system is optionally enclosed, thus creating a controlled environment, to further reduce contamination and evaporative effects.

In some embodiments, the high throughput processing systems of the invention include one or more automated systems for precisely positioning an object, as described in U.S. Ser. No. 09/929,985, entitled "Automated Precision Object Holder and Method of Using," filed Aug. 14, 2001. Microtiter plates must be placed precisely under liquid dispensers to enable a liquid dispenser, for example, to deposit samples or reagents into the correct sample wells. A tolerance of about 1 mm, which can sometimes be obtained by systems that do not include this type of automated precision object holder, is adequate for some low density microtiter plates. However, such a tolerance is often unacceptable for high density plates, such as a plate with 1536 wells. Indeed, a positioning error of one mm for a 1536 well microtiter plate could cause a sample or reagent to be deposited entirely in the wrong well, or cause damage to the system, such as to needles or tips of the liquid dispenser. Accordingly, positioning devices as described in U.S. Ser. No. 09/929,985 are also optionally included in the systems of the invention, particularly when 1536 well plates are used.

Figure 13A:
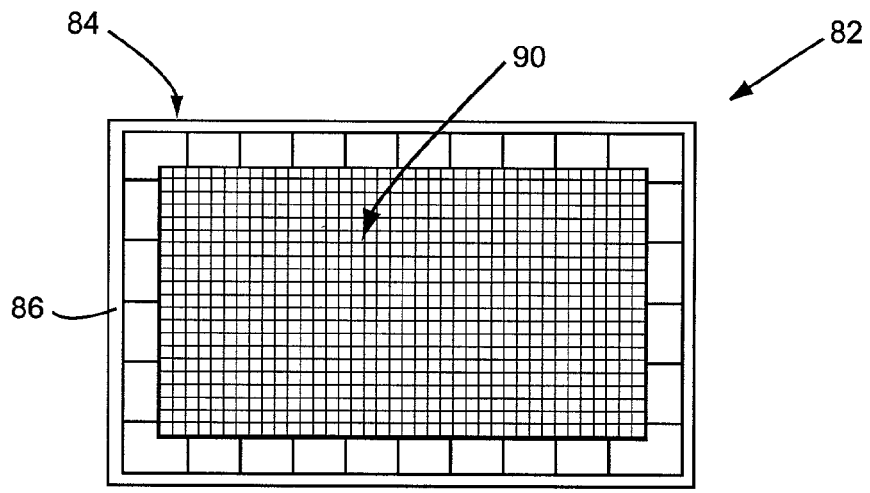
FIGS. 13A, B and C illustrate a multiwell plate useful for precise alignment.
Figure 13B:
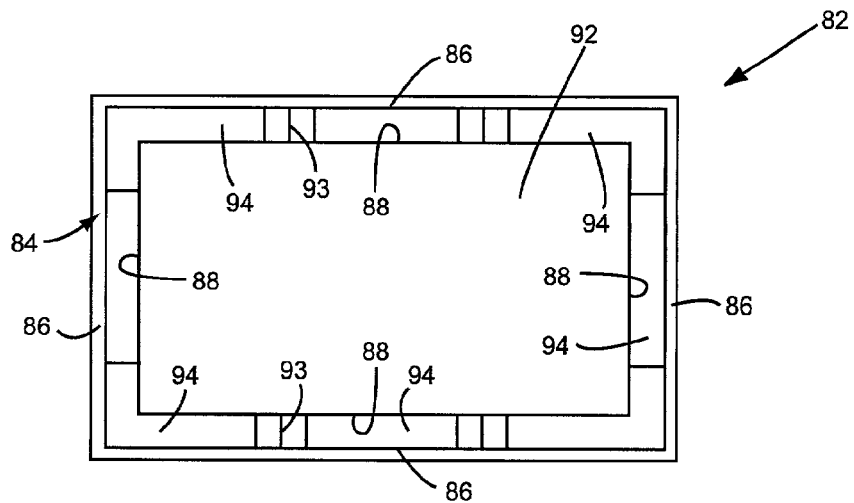
Figure 13C:
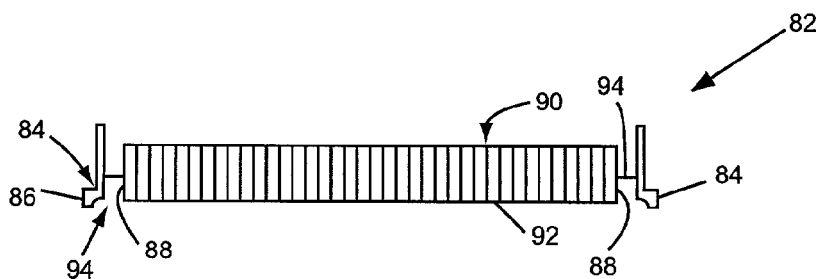
Figure 14:
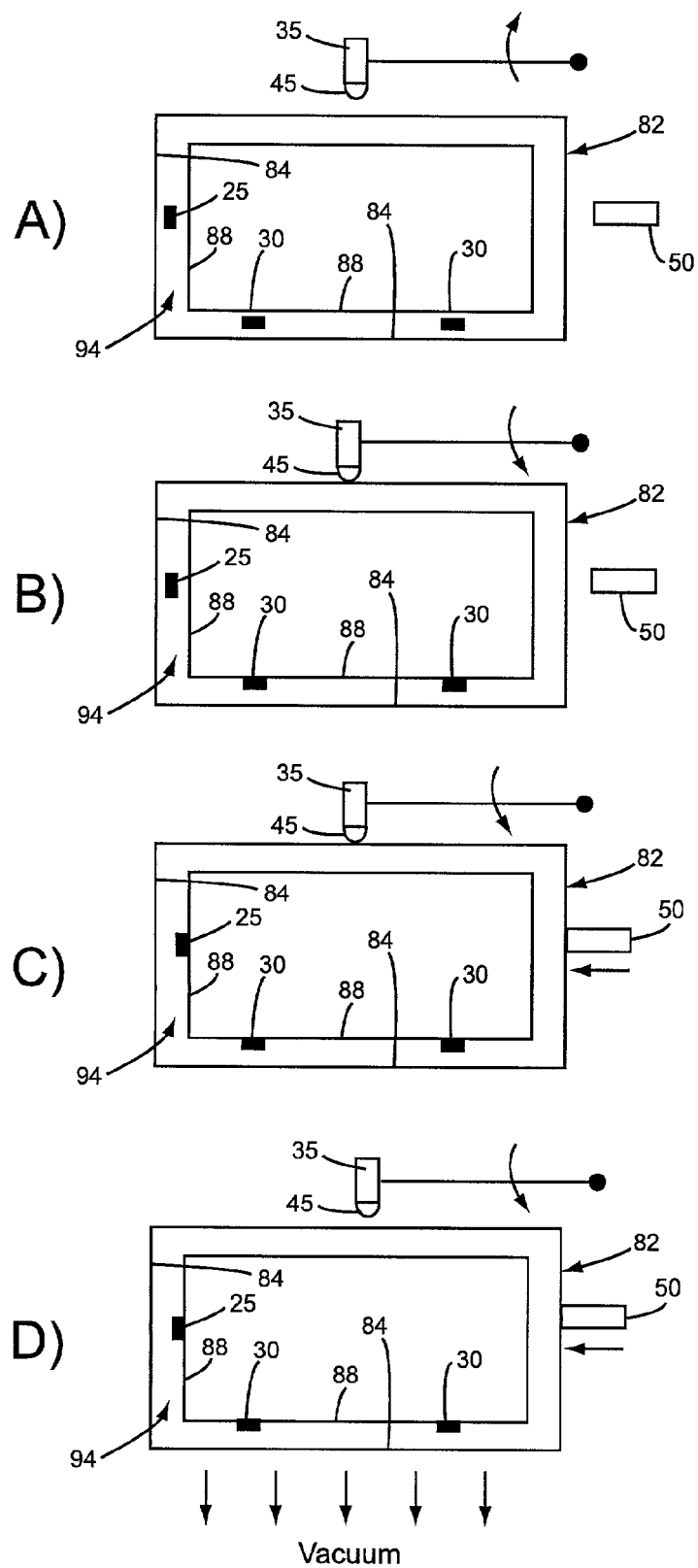
FIG. 14 illustrates a positioning device in operation, with the alignment tabs contacting the inner wall of a microwell plate, e.g., as shown in FIG. 13.

These positioning devices have at least a first alignment member that is positioned to contact an inner wall of the microtiter plate when the microtiter plate is in a desired position on the support. An inner wall 88 of a microtiter plate is shown in, for example, FIG. 13. In some embodiments, two or more alignment members are positioned to contact a single inner wall of the microtiter plate when the microtiter plate is in the desired position on the support. The use of an inner wall of the microtiter plate as an alignment surface greatly increases the precision with which the microtiter plate is positioned on the support compared to, for example, aligning the microtiter plate using an outer wall, thereby facilitating further processing of the samples contained in the microtiter plate. The positioning devices can further include at least a second alignment member that is positioned to contact a second wall of the microtiter plate when the microtiter plate is in the desired position on the support. This second wall is preferably an inner wall of the microtiter plate. The positioning devices can include: a) a first pusher for moving the plate in a first direction so that a first alignment surface of the object contacts a first set of one or more alignment members; and b) a second pusher for moving the plate in a second direction so that a second alignment surface of the object contacts a second set of one or more alignment members. In presently preferred embodiments, either or both of the pushers includes a lever pivoting about a pivot point. The lever can be operably attached to a spring or equivalent, which causes the pusher to apply a constant force to the object to, for example, move the object in the first direction against the first set of alignment members. FIG. 14 illustrates the positioner in operation, including the use of alignment tabs 30. For further information, see, U.S. Ser. No. 09/929,985.

The automated precision object holders can also include a retaining device for retaining a microtiter plate in a desired position on a support. These retaining devices can include, for example, a vacuum plate which, when a vacuum is applied, holds the microtiter plate in the desired position. The vacuum plate, in some embodiments, has an interior surface and a lip surface, with the interior surface being recessed relative to the lip surface.

Sample holders, e.g., empty multiwell plates or sample holders comprising a plurality of samples, are typically introduced into the system in one of two ways. First, they are optionally manually placed into an incubator and registered in the system, e.g., at a controller PC. Second, they are optionally introduced from a static plate hotel, e.g., that is also used for plate queuing during operation of the system.

In some embodiments, sample holders are labeled with at least one identifier or label, for example, a bar code, RF tag, color code, or other label. When the sample holders are labeled with a bar code, each robot is typically provided with a bar code reader. The bar code readers are optionally positioned on the robotic arms or any other position on the robot depending upon the application and type of sample container used. By identifying each specimen plate with a bar code, RF tag, or color code, the system can positively identify each sample holder, e.g., when retrieving, processing, or detecting each sample. In addition, the information is also optionally used to provide reports regarding assay outcomes and results, and to provide an inventory of a large number of samples, e.g. libraries of nucleic acid samples. For example, an inventory is optionally used to compare a list of desired plates with a list of plates present in the system, and notify an operator of any discrepancies.

Advantageously, when a sample holder is provided with a bar code at opposite ends, and the bar codes have indicia relating orientation, the present invention determines which end of the sample holder is facing the robot. For example, one end of the sample holder optionally has a bar code with an even code, while the opposite end of the sample holder has an odd numbered code. Accordingly, the robots of the invention easily determine whether a leading or trailing edge of a sample holder is facing the bar code reader in the robot. More advantageously, in this example, the robot reliably and consistently determines which end of a sample holder to insert into each device.

Because compound management is a fundamental part of any research institute, the integrity of the compound collections and the databases is important. Therefore, the bar codes described above or other markers or labels affixed to the sample holders are optionally used to provide a compound or sample plate inventory, e.g., that is tracked by a controller module, for the high throughput processing systems of the invention. The inventory typically keeps track of what samples and/or sample holders are in the system, as well as their location and status within the system. By providing a bar code system on the sample plates, the robotic arms are used to track the plates throughout the system. In addition, information can be transferred to a central controller, e.g., a PC, that coordinates locations with resulting data from various processes to provide an inventory combined with assay results.

Further to providing a complete inventory of samples, the present invention provides a method for plating materials using markers to track the plating procedure. For example, samples, e.g., libraries of samples, often enter the system in a 96-well format and are subsequently condensed into a single 384 or 1536-well plate. To aid in the inventory and tracking process, the transformation from a low-density format to a high density format is tracked using markers as described below.

The system described below is typically used for the specific application of condensing the contents a first set of microwell plates into a second set of microwell plates. Typically the number of wells in the second set is a whole number multiple of the number of wells in the first set of plates. For example, four unique 96-well plates are optionally condensed into a single 384-well plate in a method comprising tracking the reformatting to insure accuracy, e.g., 100% accuracy, e.g., in locating and tracking samples. The concept also applies to 384 to 1536 transformations and reverse processes. The accuracy of the database depends on knowing exactly where each 96-well plate is located within the 384-well plate after the transfer is completed. By giving the operator a simple visual check as well as providing a detector check system, the method ensures tracking accuracy.

Compounds provided in 96-well plates are typically in an 88-well format with one column empty, e.g., column 12. One column is typically kept empty so that when compounds are assayed there are blank wells, e.g., for assay controls. The entire column is not typically needed for controls but it is the standard way of plating compounds. Also used is an 80-well format in which two columns, e.g., the first and last columns 1 and 12, are left open.

The process typically starts with samples, e.g., samples stored as dry films or fluidic samples, in one or more 96-well plates in the 88-well format described above. Typically, four 96-well plates are converted up to a single 384-well plate. A marker is than added to one or more of the empty wells, e.g., well A12, in the first 96-well plate. See FIG. 11A ands 11B for labeling of wells and marker wells. The second plate receives a second marker or label, e.g., in well A12 also. The third and fourth plates, if they are used, also receive a marker in the similarly located well in those plates, e.g., well A12. Each marker used is different, e.g., a different colored dye, a different fluorescent dye, or a different concentration of fluorescent dye. The contents of the four plates (or fewer if that is the case) are added sequentially into the larger plate. If dried films are used in the smaller plates, they are typically dissolved in the smaller plates prior to transfer to the larger plate. In the larger plate, e.g., the 384-well plate to 1536-well plate, a pattern of markers results, e.g., in the upper right corner, such as in wells A23-24 and B23-24. In this manner the accuracy of the transfer is monitored. When a colored dye is used, the process is optionally monitored visually to ensure accuracy by observing whether the intended pattern is obtained. If fluorescent dyes are used, a fluorescent detector is used to monitor whether the plates were accurately transferred. In some embodiments, a fluorescent dye is used in combination with a colored dye to allow visual as well as instrument tracking of samples. In other embodiments, wells other than A12 are used for markers. Any well may be used as long as the resulting pattern is predetermined to track the transfer.

In one example, a solution of colored dye, e.g., about 0.5 mg/ml, plus a florescent dye is added to well A12 in each 96-well plate. The first plate in the transformation receives a red dye and a fluorescent dye at concentration 1×. The second plate receives a yellow dye with a fluorescent dye concentration of 0.5×, the third plate receives a green dye and a fluorescent dye at 0.25×. Finally the fourth plate receives a blue dye and a fluorescent dye at 0.125×. For example, the dye concentration is optionally an FITC solution ranging in concentration from about 0.1 mg/ml to about 0.0125 mg/ml. The contents of the four plates are then added in sequence to a single 384 well plate. In the final 384 well plate a colored pattern is formed in the upper right corner (e.g., wells A23-24, B23-24), as shown in FIGS. 11 and 12. For example, FIG. 11 illustrates four 96 well plates with markers, which are then replated into a 384-well plate as shown in FIG. 12A and then four 384-well plates are optionally replated in a 1536-well plate, e.g., in a format as shown in FIG. 12B. Each pattern in the figures is indicative of a different type of dye in the well as shown in the figure legends. As illustrated in the figures, the colors allow for the human eye to monitor the process to ensure accuracy. A simple check to determine the orientation of the colored dyes allows an operator to be sure of the plate orientation. The fluorescent dye is detected by one of various fluorescent detection instruments and allows the plating procedure to be monitored by instrumentation.

In some embodiments, the samples from one or more plates are to be mixed with the corresponding sample in one or more additional plates. In this case, the mixing can be monitored by determining the color of the dye in the marker well of the target plate. For example, if a first plate has a yellow marker and the second plate has a red marker, when the markers are mixed, the corresponding well in the target plate will have an orange marker. Similarly, if the markers are fluorescent dyes of different concentrations, the target plate will have a concentration of dye can be determined based on the amounts in the original plates and the dilution factor.

In the systems of the present invention the markers can be dispensed into a sample plate at one station location, e.g., comprising a fluid dispenser, and typically transferred into a higher well density plate, e.g., at the same station location or at a different location. The plate having the higher well density is then typically transferred to a detection station location, e.g., in the same or a different work perimeter to detect the resulting color and/or fluorescent pattern in the larger plate, e.g., the 384 or 1536-well plate. In addition, a color photograph is optionally taken or an operator optionally views the resulting larger plate to ensure the correct color pattern. Alternately, a colorometric detector is used.

Although the high throughput systems of the invention are primarily automated robotic systems, certain functionality is optionally manual. For example, an operator optionally manually introduces a particular sample holder into a high throughput screening system, e.g., by placing the sample holder onto a table device, holding area, or the like. For example, holding areas 240 and 250 in FIG. 1, are optionally used to manually introduce a sample holder into the system, e.g., into work perimeter 105 or 115 respectively. A rotational robot arm optionally retrieves the sample holder from the manual holding table or area. It is optionally moved to a storage or station location, or moved to a transfer area, such as transfer area 195 or 200, e.g., to be retrieved by a second rotational robot. The rotational robot that retrieves the sample plate from the holding area or transfer station typically moves the sample holder into any of its associated station locations, to be operated on or processed by the device associated with that station. For example, a rotational robot positions a sample holder in one of the detectors included in the system or deposits the plate into a receptacle for a dispensing device. To facilitate such manual operation, the operator typically uses a basic command set to introduce, move, and process individual sample holders. Any combination of manual and automated processes is contemplated within the present invention. However, sample holders are also optionally introduced into the system automatically, e.g., from a storage module within the system or coupled to the system. In this case, a central controller or a controller coupled to the storage module is used to direct which sample holders are introduced into the system.

G. Controllers

The high throughput screening systems of the invention typically operate under control of one or more computer systems. For example, a control unit is optionally coordinated with the operation of the high throughput system. Alternately, a single computer or multiple computers are optionally used to control and monitor the entire system or a desired portion of the system. Operator stations, e.g., including alerts, are also typically provided to allow an operator to control and/or monitor the system.

For example, FIG. 1 illustrates a control unit 320, which is optionally used to coordinate the operation of high throughput screening system 100. As operator monitoring is typically desired for such a system, an operator station, e.g., station 310 is also provided. Operator station 310 optionally accommodates, for example, operator console 315 for monitoring computer and process functionality, and operator alert 325, e.g., for alerting an operator with either a visual, audio, or pager alert. The operator console indicates, for example, what station locations and/or devices are occupied, what transfer stations are occupied, robot status, incubator status, temperature of various system components, and any other information the operator wishes to know about the system.

Operator alert 325 is optionally an automated paging system that pages one or more operators upon notice of an error condition, e.g., requesting operator intervention. Alternatively, the alert is a visual or an audible alarm. For example, a telephonic system allows a control PC to initiate calls to predetermined numbers, e.g., to telephone or pager numbers. For example, if an error condition develops during operation, the system calls a number from a predetermined list of contacts, plays a recorded message and waits for a telephone keypad response. In this manner, the system is optionally controlled and kept in operation from a remote location. The system can also include one or more cameras, e.g., a webcam, which allows the operator to view the system remotely. This can allow the operator to troubleshoot the system from a remote location.

Preferably, operator station 315 is located adjacent to one or more work perimeters, such as work perimeters 105, 115, and/or 125. In such a manner the operator not only sees operator console 315 but is also able to visually inspect robotic activity and the devices of the invention. Accordingly, components of operator alert 325 may be placed in a work perimeter or even on the devices themselves. The work perimeters are also optionally positioned distant from the operator and the operator console, with the operator alert operating to page the operator.

Figure 2:
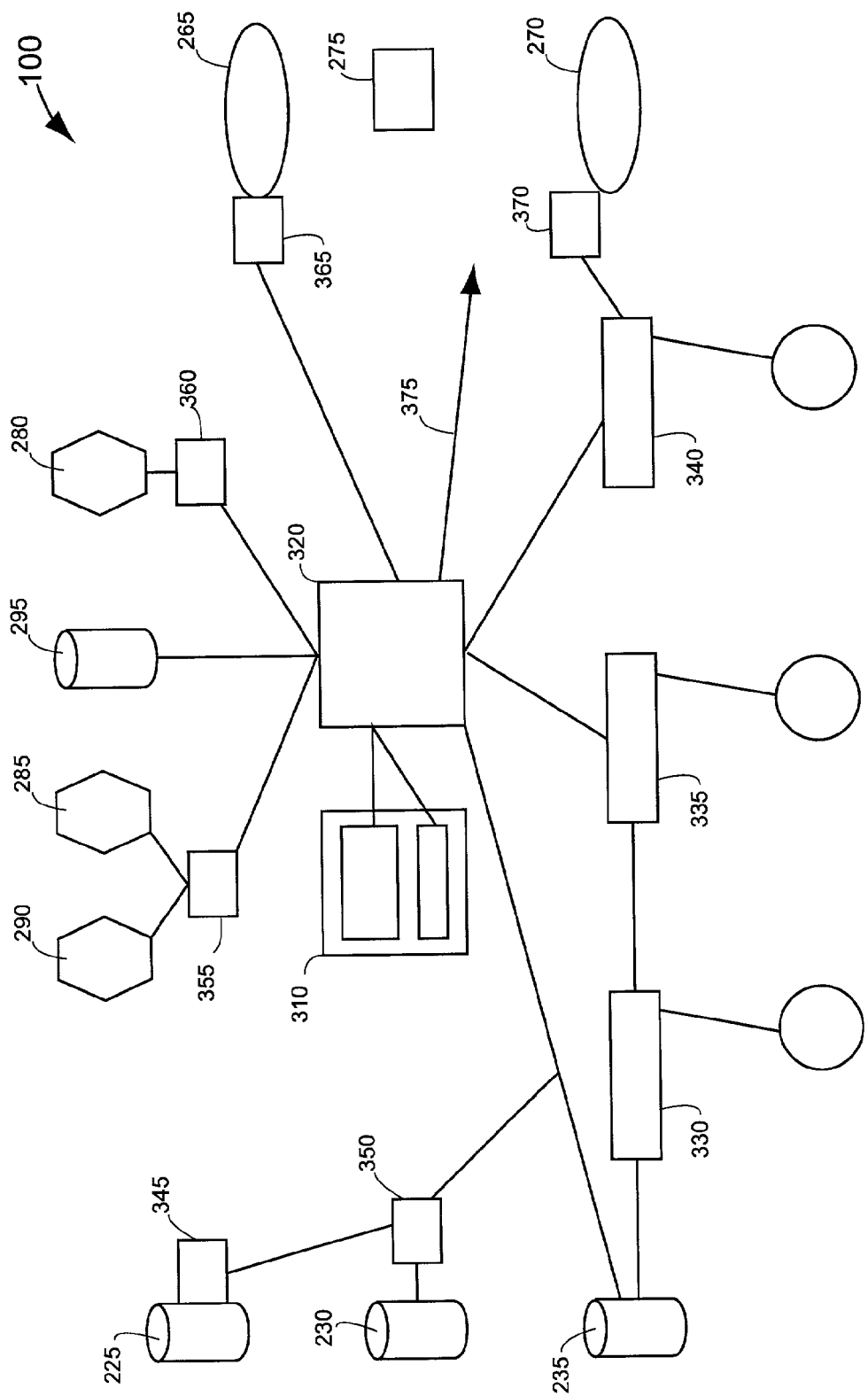
FIG. 2 is a diagram of communication links for a high throughput screening system, e.g., as shown in FIG. 1.

Referring now to FIG. 2, an example of interconnecting controllers in high throughput screening system 100 is provided. Automated instrument devices typically have an integral controller or a controller assigned to operate that instrument device. For example, instrument device 225 is shown with integral controller 345, instrument device 265 is shown with integral controller 365, and instrument device 270 is shown with integral controller 370. Also, instrument device 230 is shown with a separate dedicated controller 350, and in a similar manner, instrument device 280 is shown with separate dedicated controller 360. For some instrument devices, a single controller operates more than one instrument device. For example, instrument devices 290 and 285 are shown under the control of controller 355. Any controller devices and configurations known in the art are contemplated within the present invention.

The controllers not only operate the devices of the invention, but also typically off-load processing from a system controller, e.g., controller 320. For example, in one embodiment, instrument device controllers collect and analyze data and send summary data information to a system controller. In such a manner, data communication requirements and bandwidths are reduced, thus requiring lower speed and therefore less costly communication connections. Some instrument devices, such as instrument device 235 and instrument device 295, optionally do not have a separate station controller, but are instead controlled directly from a system controller, e.g., controller 320. Also, an individual station optionally takes direction and passes data to more than one controller. For example, instrument device 235 optionally receive operational direction from robotic controller 330, but also passes data back to the central controller 320.

Although most of the communication links shown in FIG. 2 are shown as point-to-point connections, other types of connections are optionally used, such as network, Ethernet, wireless, or multi-drop connections, such as the multi-drop connection shown between system controller 350 and system controller 345. Further, instrument device and system controllers can be physically configured and connected in other arrangements known to those of skill in the art.

Preferably, each rotational robot has its own robot controller. For example, robot controller 330 controls robot 135, robot controller 335 controls robot 140, and robot controller 340 controls robot 145. Although FIG. 2 shows each robot controller directing a single robot, a single robotic controller also optionally controls multiple robots. Conversely, multiple robotic controllers can cooperate to control a single robot, e.g., controlling a carousel and reach associated with each robot. For example, robotic controller 330, which is primarily responsible for controlling robot 135, optionally accepts input from robotic controller 335 which can effect robotic movements. The robotic and system controllers are also optionally configured in other physical and logical arrangements.

In the example illustrated in FIG. 2, each robotic controller 330, 335, and 340 is preferably connected to system controller 320. System controller 320 is connected to operator console 315 located at operator station 310. System controller 320 also communicates to operator alert 325. Operator alert 325 is, for example, an automated paging system that pages one or more operators when an error condition occurs. Further, operator alert 325 optionally includes lights and audible signals for providing warnings and alerts to operators and technicians in the area. For example, a light bar having color-coded lights is optionally positioned adjacent to key devices. In such a manner, an operator receives a quick visual indication of process status.

Further, system controller 320 accepts instruction and passes data to other systems, e.g., via central system link 375. This link is optionally an internet link, a wireless link, or a local area network link such as an Ethernet system. Other links, e.g., electronic, optic, magnetic, or otherwise known in the art, are used to link system controllers. Advantageously, system controller 320 provides input to a centralized control and data collection facility and receives software and operational updates from a remote source. For example, establishing a web link provides alert and status information.

In one embodiment, the system and robots are typically programmed in AIM and/or V+. Each robot typically has a controller that is typically DeviceNet and Ethernet compatible. For example, the controllers are accessed via DeviceNet back to a Controller PC, which is typically a Pentium III, IV, or other appropriate, e.g., faster, computer known to those of skill in the art. In addition to motion of the robot, the robot controllers are responsible for all motion within a designated work perimeter or station.

Software for the PC is typically written in Microsoft Visual C++, e.g., version 6.0, or other programming language known to those of skill in the art. The controller PC is typically used to coordinate the entire system, e.g., providing high level coordination that reports and acknowledges all faults and/or errors, and provides user interface functionality. The PC also typically acts as a data concentrator, recording all data, e.g., in an Oracle format, and optionally processing such data. Alternatively, the data is stored for future processing, e.g., on another PC.

The controllers and controller links described above are used with any system as described above or those examples provided below. In addition, various methods of using the system and the controllers are discussed below.

H. Example Systems

In the embodiment illustrated in FIGS. 1-7, high throughput screening system 100 includes three work perimeters. The first work perimeter 105 is generally directed to the task of storing samples or compounds. The second work perimeter 115 is generally directed to processing samples by, for example, adding reagents, shaking, or incubating. The third work perimeter 125 is generally directed to analyzing the samples, for example, by detecting the samples, or measuring physical properties of the samples. Although the disclosed example has three work perimeters defined, fewer or more work perimeters are optionally utilized depending upon application specific requirements. Advantageously, there is no particular order that must be followed in transporting samples from one work perimeter to another work perimeter because of the multi-directional utility of the present invention. For example, a sample may be processed in work perimeter 105, transported to work perimeter 125 for detection, and transported back to work perimeters 105 and 115 for further processing.

Although each work perimeter is generally directed to a particular type of task, the functionality for each work perimeter may overlap with the functionality of other areas. For example, the area generally directed to storing compounds may also perform certain functions related to processing, detecting or other type of sample property determination.

In the high throughput system 100 disclosed in this example, samples are typically stored, processed, and detected using specimen plates, e.g., 96, 384, 968, or 1,536 wells. For example, plates 210, 205, and 215 as shown in FIG. 1.

Each disclosed work perimeter 105, 115, and 125 has an associated rotational robot. For example, work perimeter 105 has rotational robot 135, work perimeter 115 has rotational robot 140, and work perimeter 125 has rotational robot 145. Each rotational robot preferably rotates about its rotational axis close to a full 360 degrees. Further, each robot preferably adjusts vertically and horizontally to align relatively higher or lower work positions. In a preferred embodiment, each rotational robot is a Stäubli RX-60 robot that is pedestal mounted.

Preferably, each rotational robot has a robotic arm that optionally extends or retracts from the robot's rotational axis. For example, robotic arm 150 and robotic arm 155 are both shown in FIG. 1 in a moderately extended position. Robotic arm 160, however, is shown in FIG. 1 in an extended position. Accordingly, each rotational robot has an associated rotational reach. For example, robot 135 has rotational reach 105, robot 140 has rotational reach 115, and robot 145 has rotational reach 125. Although the rotational reach patterns are shown to be generally circular or oval, the rotational reach can accommodate other geometries.

A transfer station is preferably positioned between each adjacent work perimeter. In one embodiment, the transfer station provides a temporary area for positioning sample holders to facilitate moving a sample holder in or out of an area. For example, transfer station 195 is positioned between work perimeter 105 and work perimeter 115. In a similar manner, transfer station 200 is positioned between work perimeter 115 and work perimeter 125. Although transfer stations 195 and 200 are shown centered between adjacent work perimeters, the transfer station may be relatively closer to, or even within, a work perimeter. The transfer area is also optionally positioned where adjacent robots directly pass a sample holder from one robot to the adjacent robot.

Preferably, each robotic arm has a robotic gripper. For example, robotic arm 150 has gripper 165, robotic arm 155 has robotic gripper 170, and robotic arm 160 has robotic gripper 175. In this disclosed example, each robotic gripper 165, 170, and 175 is configured to removably couple with a specimen plate, such as standard 384 or 1,536 well plates. Robotic arms 150 and robotic grippers 170 are optionally operated pneumatically, magnetically, or by other means known in the art.

The robotic grippers of the embodiment illustrated in FIG. 1 are configured to removably couple to specimen plates, such as specimen plates 205, 215, and 220. To transfer between adjacent work perimeters, a first robot retrieves a specimen plate, positions the plate into a transfer station, and then a robot from an adjacent work perimeter retrieves the plate from the transfer station. For example, FIG. 1 shows sample plate 215 positioned in transfer station 195. Accordingly, either robot 140 or robot 135 can engage and use specimen plate 215. In a similar manner, FIG. 1 shows robot 145 either returning specimen plate 220 to transfer station 200 or retrieving specimen plate 220 from transfer station 200 and transporting specimen plate 220 for further processing, measurement, or detection.

Work perimeter 115 also provides incubator device 290 which can be, for example, set to provide the proper conditions for facilitating growth of cellular material. Due to the particular environment within the incubator, the incubator may have a sealed door 300, provided, for example, by an airlock. Accordingly, sealed door 300 preferably has a gripping structure 305 coupled to robotic gripper 170. In such a manner, robotic arm 155 can position robotic gripper 170 adjacent to the gripping structure 305 and open and close door 300. As the robot must open and close door 300, preferably a temporary holding area 260 is positioned adjacent to incubator 290 for temporarily holding a specimen plate as it is moved into or out of incubator 290.

In the illustrated embodiment, work perimeter 125, which is primarily directed to analyzing samples, comprises detector 265 and detector 270, e.g., fluorescent detectors. After the specimen plates have been detected in either or both detectors 265 and 270, the specimen plates are optionally returned to a storage facility, such as storage facility 230, or may be deposited in a container device 275 for disposal or reuse.

Referring now to FIG. 3, the specific configuration of a variety of work perimeters will be further addressed. In the illustrated example, high throughput screening system 100 provides configuration flexibility by, for example, providing a plurality of station locations within each work perimeter. For example, work area 110 contains station locations 380, 385, 390, 395, 400, and 405. Work area 120 includes station locations 410, 415, 420 and 425, while work area 130 contains station locations 430, 435, 440, 445, 450, and 455. Although high throughput screening system 100 only defines a select number of station locations, more or fewer station locations are optionally defined depending upon the reach of each robotic arm and the size of selected devices. Further, station locations are optionally added, moved, or removed depending on specific application needs.

Devices for performing process steps are typically selected according to specific application requirements. After selection, each device is assigned to a particular station location within a work perimeter. For example, device 225 is assigned to station location 380, while device 230 is assigned to station location 385.

Because station locations remain the same irrespective of what device is positioned in that station location, the high throughput screening system 100 is easily reconfigured to accommodate a variety of specific needs. For example, FIG. 3, when compared to FIG. 1, shows that a new station location 390 was defined and holds a new storage device 232. FIG. 3 also shows that station location 400 has been reconfigured to have incubator 237 replace compound storage device 235. Further, work area 120 has had incubator 290 removed from station location 410. Accordingly, the high throughput screening system 100 is reconfigured to add, delete, or replace devices in any station location. Advantageously, station locations are optionally added or removed to accommodate changes in the area or robot orientation. Not only is the system thereby flexibly reconfigurable, but the system easily adjusts to accommodate adjustments in work flow.

Figure 8:
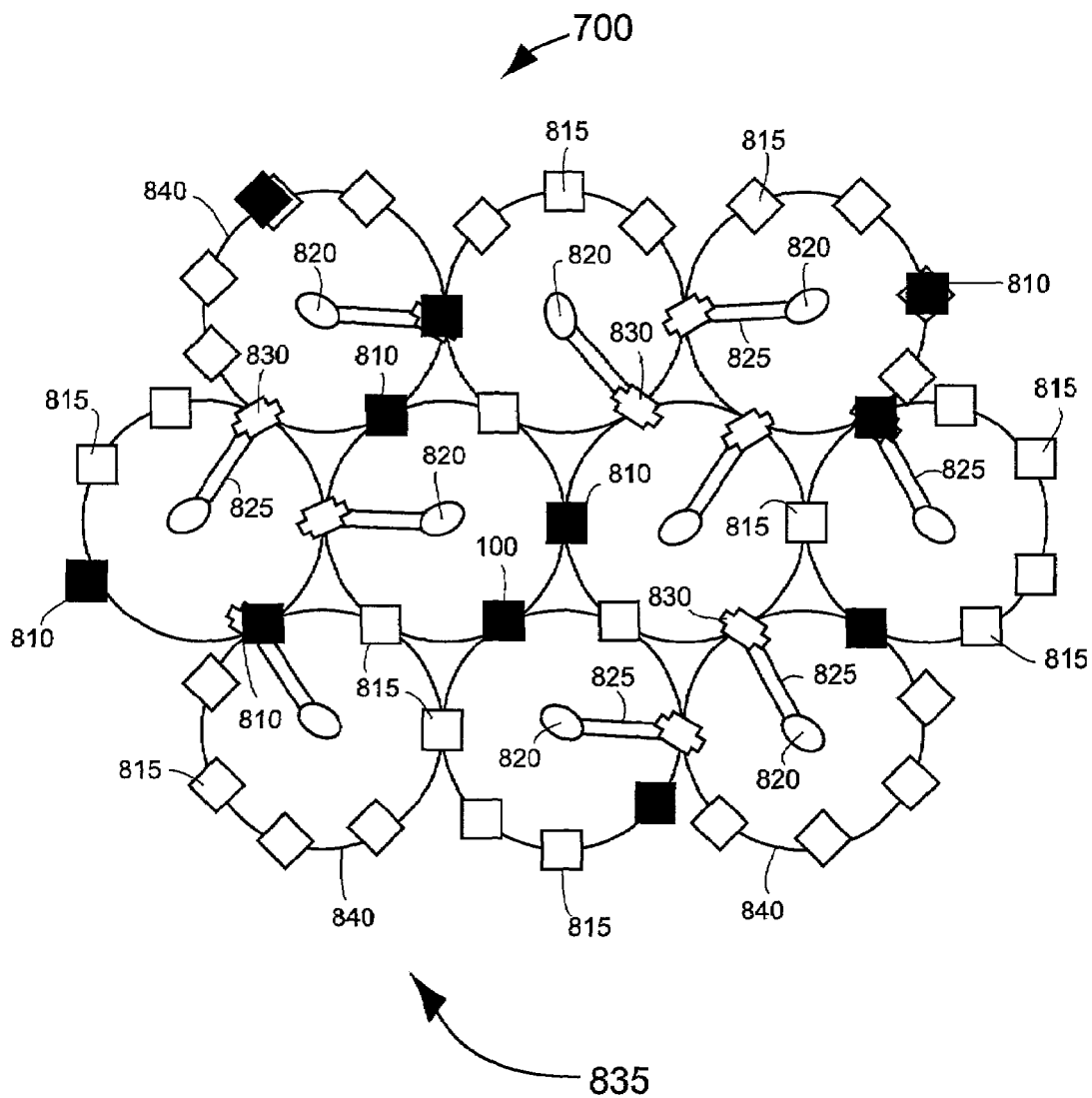
FIG. 8 is a diagram showing station locations of a non-linear processing system in accordance with the present invention.

In another embodiment, the robotic work perimeters are arranged in a substantially honeycomb configuration that permits a non-linear processing system 800, as shown in FIG. 8.

In this non-linear processing system, specimen plates 810 are moved, e.g., from a first station location 815 to a different station location 815, e.g., in a non-linear fashion. This setup optimizes throughput of the overall system by permitting sample holders, e.g., specimen plates 810, to be moved to the closest appropriate station rather than through a series of stations. In non-linear processing system 800, a plurality of rotational robots 820, are provided, each having a rotating robotic arm 825 ending with a robotic gripper 830. The robots are positioned within a rotational reach 840 of each other. The rotational reach 840 of each robotic gripper 830 defines a circle and each robot 820 is positioned so that the circles defined by the robotic grippers 830 intersect at several points. At these intersection points and at other points around rotational reach 840 of each robotic gripper 830, station locations 815 are located. Station locations 815 are configured to accept specimen plates 810 and/or to conduct procedures or processes on specimen plates 810. For example, any station location 815 optionally stores, processes, and/or detects the samples in specimen plate 810. A station location 815 is also optionally used to perform reagent additions, PCR, purification, filtration, washing, transfer of samples to new plates, vacuum/pressure treatment, light/UV exposure, and/or sample removal/addition.

In non-linear processing system 800, shown in FIG. 8, a specimen plate 810 moves from one station location 815 to other station locations in a non-linear fashion thereby allowing a higher throughput. In addition, this arrangement of rotational robots 820 with accompanying robotic arms 825 and robotic grippers 830 is optionally used to efficiently assemble devices, e.g., medical devices or electronic devices. Because process steps sometimes require a device to be cured, incubated or otherwise processed in a manner that requires a specific time, a non-linear processing system 800 optionally comprises nesting stations as part of a station location 815. In contrast, a linear processing system requires the device to pass down a linear pathway while it is being cured or otherwise processed. In a non-linear processing system, the device can be left at a station location 815 and then when required, a robotic gripper 830 moves the device to the next desired station location 815, which is optionally any station location in the system. In this way, extremely efficient and high throughput processing systems is provided.

Figure 9:
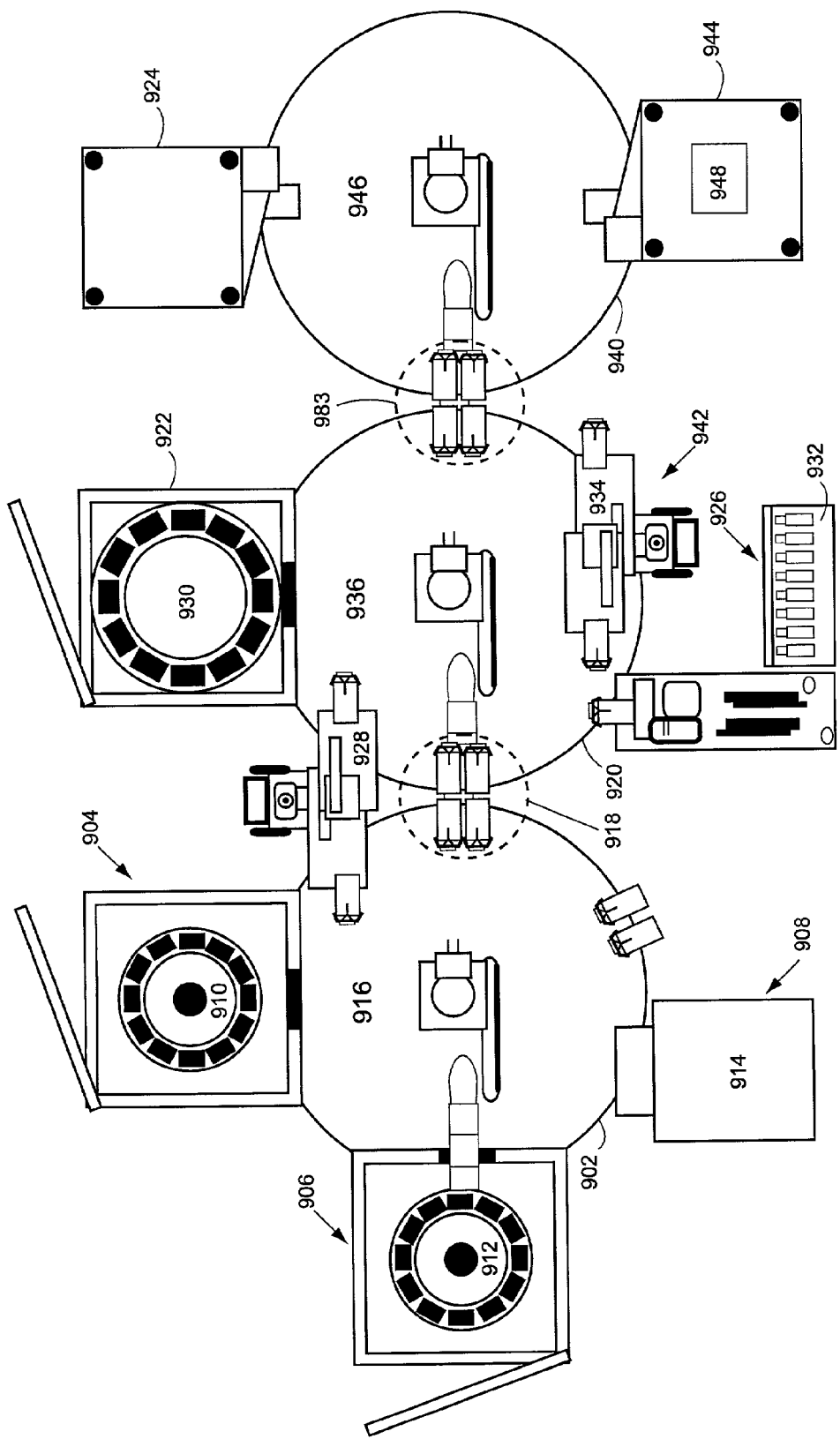
FIG. 9 illustrates an example high throughput processing system of the invention.

FIG. 9 illustrates an example high throughput processing system of the invention. For example, system 900 comprises three work perimeters, 902, 920, and 940. Each work perimeter is associated with a rotational robot, e.g., rotational robots 916, 936, and 946. Two transfer stations, stations 918 and 983, are provided to bridge the area and provide transport between work perimeters 902, 920, and 940. Work perimeter 902 comprises three station locations, e.g., 904, 906, and 908. Station location 904 comprises compound incubator 910 and station location 906 comprises compound incubator 912. A miniprep device, e.g., device 914, such as a Tecan Miniprep, is positioned in station location 908. Work perimeter 920 comprises three station locations, e.g., 922, 924, and 926. Station location 922 comprises assay plate incubator 930 and station location 924 comprises a Hydra 384, device 934. A Cartesian Synquad, e.g., device 932, is positioned in location 926. In addition, a Hydra workstation device, e.g., device 928 is positioned at a station location proximal to both work perimeter 902 and work perimeter 920 and is accessible by either robot 916 or robot 918. This device can thus function as a transfer station to transfer sample aliquots from a sample plate in work perimeter 902 to an assay plate in work perimeter 920. A pin tool can also be used for this purpose in place of the Hydra. Work perimeter 940 comprises two station locations, e.g., locations 942 and 944. Station location 944 comprises a LJL Acquest plate reader, e.g., device 948. Station location 942 is left empty in the example, but is optionally fitted with a device at any time, e.g., before or during operation of the device, e.g., as needed.

Many other embodiments are also available in the present invention. For example, a system optionally comprises ten station locations occupied as follows: two compound libraries, 2 plate interchange platforms or transfer stations, an incubator, 2 liquid handling devices, 2 plate readers, and a mini-prep station. These stations are optionally divided into two or three work perimeters. Other combinations other devices, and different numbers of devices are also optionally used for various processes, e.g., as described in more detail below.

Figure 10:
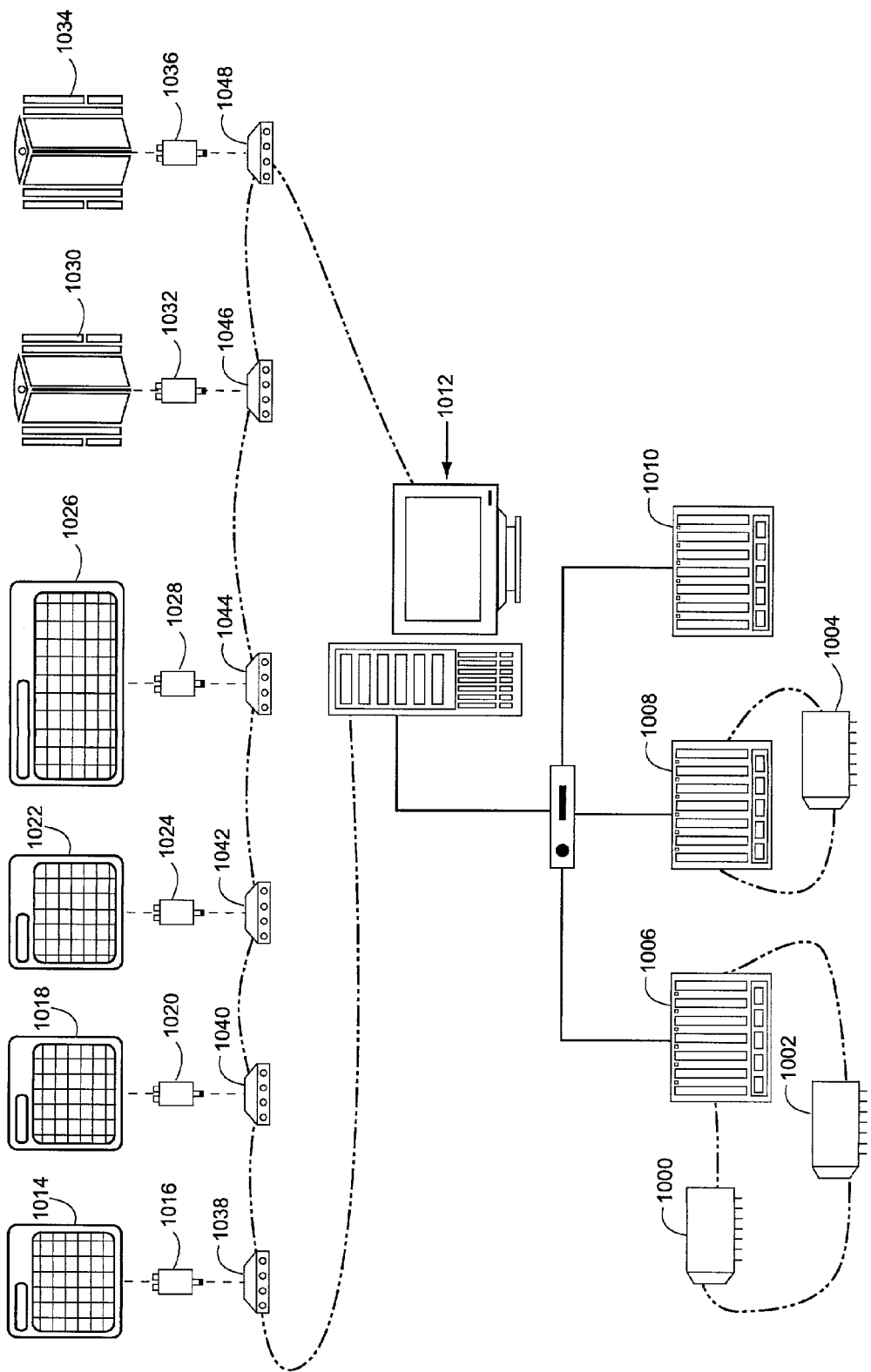
FIG. 10 illustrates a communication diagram for the system shown in FIG. 9.

FIG. 10 illustrates the control hardware used for the above configuration comprising ten stations or devices. In FIG. 10, three robot controllers are used, e.g., controllers 1006, 1008, and 1010, one for each robot in the system, e.g., to handle all motion control. Each robot controller is typically DeviceNet and Ethernet compatible. Plate carousels and incubators each have a controller, e.g., first carousel dial 1000, second carousel dial 1002 and incubator dial 1004. In addition, each piece of peripheral hardware optionally has its own controller, e.g., with an RS-232 interface to Device Net. For example, Tecan Mini prep 1014 has liquid controller 1016 and an RS232 DeviceNet protocol converter, e.g., converter 1038. Likewise for Hydra 96 1018 and Hydra 384 1022, which are controlled via controllers 1020, 1024, with converters 1040 and 1042. A liquid handler is also typically controlled using its own liquid controller, e.g., Cartesian liquid handler 1026 with controller 1028 and converter 1044. The plate readers, e.g., 1030 and 1034, are also connected to controllers, e.g., controllers 1032 and 1036 and to the central system via converters 1046 and 1048. All controllers are accessed, e.g., via DeviceNet, to supervisor PC 1012, which is typically a Pentium III 600 MHz or faster machine. Other control hardware and devices set ups are also optionally used in the systems provided. The above is only one of many possible examples for use in the methods described below.

II. High Throughput Processing Methods

The present invention provides high throughput processing systems and methods of using such systems. In general, the systems above are used to process a number of samples, e.g., simultaneously or sequentially. Processing typically refers to screening, testing, building, or the like. For example, a library of drug candidates is optionally screened or tested for efficacy or an electronic or medical device is constructed. A typical process comprises screening a number of a biochemical or chemical compounds.

The samples are typically contained in sample holders, such as microwell plates or specimen plates, which are transported through the system by rotational robots. For example, a robot optionally retrieves a sample plate from a storage module in a first work perimeter, transports the sample holder to a second work perimeter for processing and then to a third work perimeter for detection and analysis.

The sequence of steps performed in a given process is typically specified, e.g., by an operator. The order of the steps need not follow a linear path through the system and need not involve each device of the system in a sequential manner. Each device of the invention is optionally accessed as needed and the devices are optionally used in a nonsequential or random order. For example, a sample holder is optionally transported from a first device to a second device to a third device and then back again to the first device, e.g., for further mixing or incubating prior to detection, e.g., at a fourth device. In addition, the order followed for transporting a sample holder through the system need not be the same each time the system is used. The order is changeable and is typically directed at the beginning of each assay, e.g., by an operator. In addition, upon receipt of the assay status, an operator optionally changes the assay and directs a new path for a sample holder in response to the information.

In one embodiment, the invention is used to screen a plurality of samples. A screen is typically a test that is conducted on a number of specimen plates, and may include multiple steps. A screen is performed by operating a defined method on a given set of specimen plates. Using the high throughput systems of the invention, an unprecedented amount of samples are optionally processed and screened simultaneously, serially or in parallel, including screening arrayed libraries of chemical entities such as small molecules, combinatorial chemical compounds, synthetics, natural products, extracts, drugs or drug candidates, nucleic acids, short oligonucleotides, anti-sense oligonucleotides, single-stranded DNA, RNA, double stranded DNA, RNA, RNA/DNA hybrids, triplexes, proteinaceous substances such as wild-type and synthetic proteins, peptides, both natural and synthetic, antibodies, Fab fragments, antibody epitopes, constrained peptides, protein fragments, dominant-negative and dominant-positive proteins, mutated proteins, synthetically modified proteins, as well as expressed sequence elements including eukaryotic and prokaryotic expression cassettes, retroviruses, adenoviruses, CMV, SV40, Tn10 driven full length cDNAs, DNA fragments, peptides, truncated proteins, and the like. For example, see e.g., published PCT application PCT/US98/27233 (WO 99/32619) for information regarding double stranded RNA molecule (RNAi) methods for modulating gene expression.

Samples for these screens are optionally derived from synthetics derived from laboratories or engineered organisms, as well as those obtained, extracted, cloned, or expressed from naturally occurring species including, but not limited to, mammalian species (e.g., human, mouse, rat, rabbit, goat), eukaryotes including *Drosophila*, yeast, *C. elegans*, prokaryotes including bacterial strains, and plants such as algae, aloe vera and arabidopsis, among others. Additionally, the present systems are useful for screening whole organisms, especially microorganisms such as bacteria, yeast, c. elegans, and parasites such as malaria, and viruses (i.e., hepatitis and other flaviridae, retroviruses, adenoviruses, and viroids). In one embodiment, the present invention screens combinations of these organisms or entities, either serially or in parallel to test their influence on a particular biological test or assay.

In this manner, any type of screen is contemplated within the present invention, and in particular, screens for agonists/antagonists, natural and synthetic, e.g., for G-protein coupled receptors, kinases, proteases, phosphatases, and transcription; agonists/antagonists of cellular, neuronal, hepatic, tumor cell differentiation, and retrodifferentitation; agonists/antagonists of viral and parasite mechanisms of entry, replication, exit, and pathogenesis; agonists/antagonists of immune cell activation, inactivation, energy, migration, or apoptosis; and agonists/antagonists of protein-protein interactions important in immunology, cardiovascular, signaling biology, metabolic disease, diabetes, osteoporosis, and other disease areas, e.g., as determined by synthetic and engineered reporter readouts using cell-free, cellular and organismal targets.

Methods of using the above described systems for a particular screen are described in more detail below, e.g., methods of designing and performing screens. For further information on various types of screens that are optionally carried out using the systems and methods of the invention, see, e.g., U.S. Ser. No. 60/275,266, entitled "Identification of Cellular Targets for Biologically Active Molecules," filed Mar. 12, 2001; U.S. Ser. No. 60/275,148, entitled "Chemical and Combinatorial Biology Strategies for High Throughput Gene Functionalization," filed Mar. 12, 2001; U.S. Ser. No. 60/274, 979, entitled "Cellular Reporter Arrays," filed Mar. 12, 2001; and U.S. Ser. No. 60/275,070, entitled Genomics-Driven High Speed Cellular Assays," filed Mar. 12, 2001. For example, U.S. Ser. No. 60/275,070 describes screens designed to identify gene regulatory regions and producing libraries of gene regulatory regions. U.S. Ser. No. 60/275,148 describes, e.g., methods for screening genes for a variety of functions, e.g., disease related functionality.

A. Designing a Process for use in a High Throughput System

Figure 4:
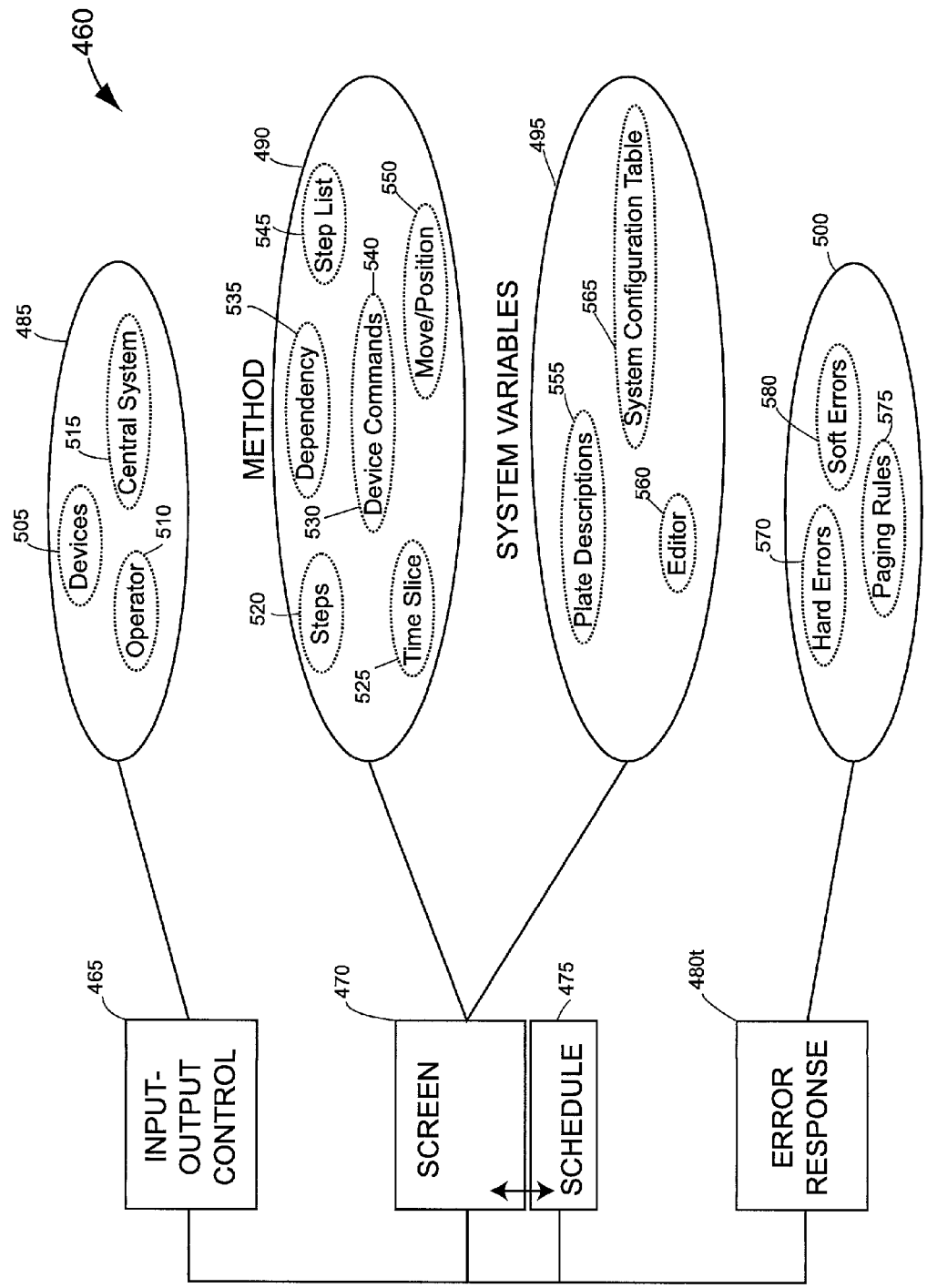
FIG. 4 is a block diagram showing software architecture in accordance with the present invention.

As described above, the systems provided herein are optionally used for a variety of different processes, e.g., screening processes, which are described in more detail below. In general, the system relies on a modular approach to defining the process. Such an approach not only enables logical development of screens, but also facilitates reusability of method modules and supports rapid reconfiguration of the system. Modular development of methods provides substantial flexibility in defining process steps, and facilitates reuse of steps and methods. Accordingly, FIG. 4 illustrates software architecture, e.g., for a high throughput screening system. Although other industries also optionally benefit from other arrangements of a high throughput system. The embodiment illustrated is primarily directed to operating screens for biotechnology or biomedical industries. For example, FIG. 4 shows that screen 470 includes and is defined by combining information in method module 490 and system variable module 495.

Methods are also typically defined in a modular manner, with a method defining and organizing individual process steps, e.g., using rules and directions. More specifically, a method is defined as if the method were to be executed on a single sample, which simplifies method definition.

Preferably, after method steps have been defined, the operator indicates the sample plates on which the method is to operate. In a similar manner, the operator optionally defines a plate or a series of plates on which the method is not to be operated. This permits the operator to define selected plates for control plates or as exception plates. Accordingly, defining methods and screens is a logical and efficient process.

Typically, a screen is defined by a method or combination of methods. In FIG. 4, for example, in screen 470, method 490 defines a set of individual steps 520. Preferably, each step is a discrete stage in a method, and is usually associated with a specific device. Because these steps typically operate on specific devices, the method also optionally incorporates specific device commands 530. In one embodiment, these steps are defined to operate on a specific class of instruments. For example, steps can be configured to "dispense 100 nl" or "aspirate 500 nl". Accordingly, each step is typically defined to address specific desired functionality from a class of instruments. During execution of the method, a device drive, e.g., device drive 505, generates the low-level commands necessary to drive a specific model of the instrument actually configured into the system.

Figure 5:
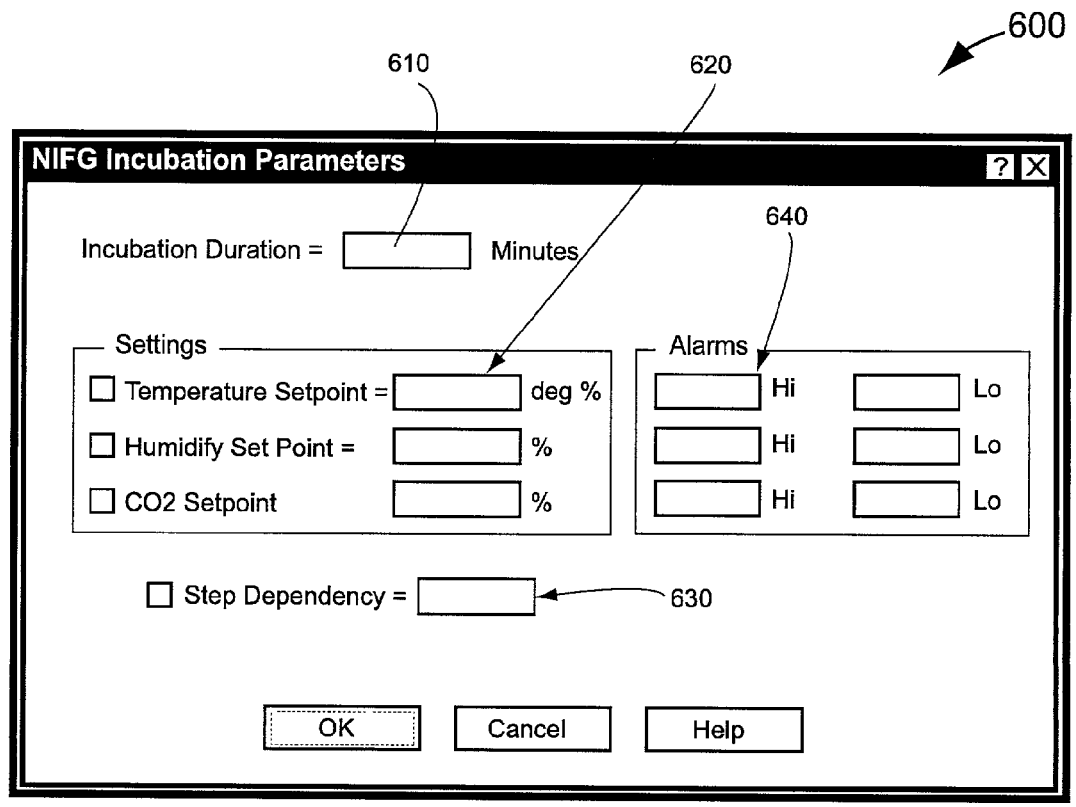
FIG. 5 illustrates an input screen for defining a step in a method in accordance with the present invention.

For example, FIG. 5 shows an example of an input screen, screen 600, e.g., for defining a step for an incubator. The screen uses a graphical user interface and permits the operator to easily define incubator duration 610, settings 620, dependencies 630, and alarms 640.

Steps 520 are optionally combined or arranged, e.g., in one or more step lists, e.g., step list 545, for performing steps in a sequential manner. However, the sequential order need not follow a predetermined order dictated by the physical setup of the devices in the system. Any device is accessed at any point in the sequence, thereby allowing the assay alone, rather than the physical setup of the system, to dictate the sequence of the step list.

Further, the start or pace of one step optionally depends on the result of one or more other steps. Therefore, the method allows dependencies 535 to be declared. In such a manner, the step list is optionally interrupted or paused until prerequisite dependencies are met. This not only simplifies defining methods, but also enables steps to operate in parallel, thereby increasing throughput efficiency.

Furthermore, any number of screens and/or methods are optionally performed simultaneously, serially, or in parallel. For example, a high throughput system of the invention optionally performs three screens, e.g., in parallel, operating multiple methods simultaneously. For example, an operator optionally defines the three screens with priorities for certain steps. For example, the operator initiates screen one, which begins with a dispensing step followed by an incubation step, another dispensing step, another incubation step, and a detecting step. Screen two includes a dispensing step, another dispensing step, an incubation step, an aspirating step and a detecting step. Screen three entails a dispensing step, a detection step, a dispensing step and another detection step.

A controller system typically coordinates the robots and/or robot controllers to preserve the priorities programmed in each screen. For example, a specimen plate A is optionally incubating in screen one. In parallel, a specimen plate B has undergone a dispensing step and another dispensing step in screen two, and must wait for the incubation station now occupied by specimen plate A. The controller system \directs the appropriate robot controller to move specimen plate B to a temporary holding area until specimen plate A has completed its incubation. In this manner, a specimen plate C undergoing screen three can utilize the dispensing station that was formerly occupied by specimen plate B in screen two. As a result, multiple screens are run at the same time, thus maximizing the efficiency and throughput of the overall system with minimal human intervention.

Figure 6:
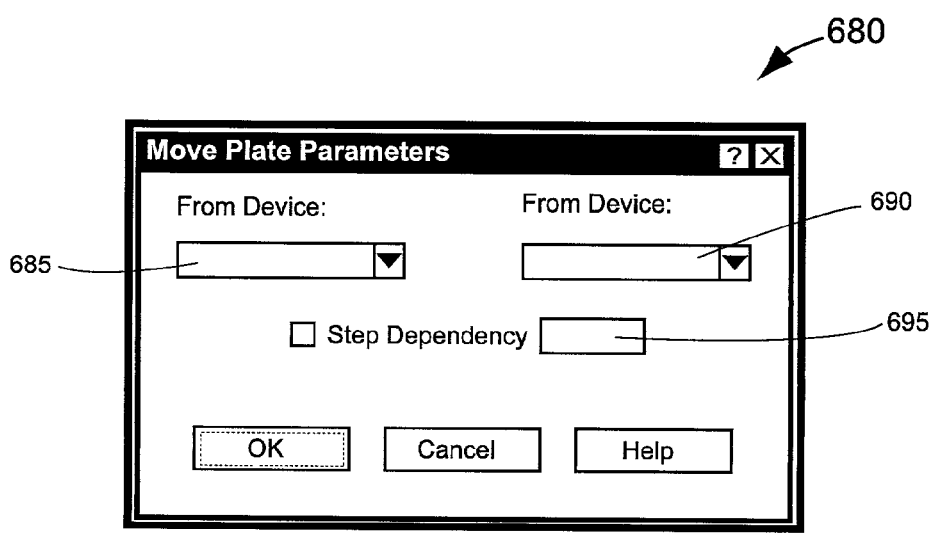
FIG. 6 illustrates an input screen for defining a move for a method in accordance with the present invention.

Referring again to FIG. 4, method 490 not only performs steps on individual instrument devices, but also accounts for moving specimen plates between instrument devices, between work perimeters, and to and from holding areas. Therefore, method 490 includes move/position information 550. FIG. 6 illustrates a preferred input screen, screen 680, for defining a move step. A graphical input screen allows the user to select a "from" device 685 from a pull down menu, and a "to" device 690 from another pull down menu. Preferably, dependencies 695 are typically set such that they must be satisfied before the move occurs. Typically, moves are defined from device to device, independent of either devices' station location. Only later, as the method is compiled or run will the system associate a physical location with each device so robotic moves are determined. And thus advantageously, the physical location of devices can be changed without affecting defined methods.

Further, many samples are time, temperature, and moisture sensitive, so the processing times are typically monitored. Accordingly, method 490 allows for a default or defined time slice 525. Time slice 525 defines the maximum time that a specimen plate can be in transition between devices. For example, if the time slice is set at five minutes, then the maximum time a specimen plate can be in transport between devices would be five minutes. If such time is exceeded, then an error condition occurs and the specific specimen plate would be identified as a reject. Preferably, this error condition triggers an operator alert. Alternatively, the rejected specimen plate is moved, e.g., to a receptacle and/or disposed.

Screens also optionally consider information captured in the system variables, e.g., variables 495 in FIG. 4. For example, plate descriptions 555 define which specimen plates are active in the system, e.g., and log that information into a central inventory, and associate specimen plates with particular bar codes, if present. The plate descriptions 555 can be modified using the editor 560. Plate descriptions also include such information as the number of wells and plate dimensions. By editing plate description 555, an operator optionally introduces new plates into the system, or requests that certain plates be removed from the system. Further, an operator defines which specimen plates are used in a particular screen, for example, by setting a range of plates to be used or setting a location from which top retrieve plates.

The system variables 495 also optionally contain system configuration table 565. Preferably, system configuration table 565 associates particular station locations to specific devices. Accordingly, system configuration table 565 provides the logical association of a device to a physical location. In a preferred embodiment, steps are typically defined to operate on devices, which are logically identified. As long as a device is consistently identified with the same logical identifier, the device can be physically positioned in any available physical location. In such a manner, a device can be moved to a new station location in a rapid and convenient manner without disturbing the method or developing a new screen.

For example, a device is optionally physically moved from a first physical station location to a second physical station location. As an illustration, e.g., in FIG. 3, storage device 295 at station location 425 is optionally moved, e.g., 180° in relation to work robot 140, e.g., to station location 410. Editing the system configuration table 565 records the physical change, e.g., now associating station location 410 with device 295. Since the system controller still identifies the device with the same logical identifier and not the physical station location, the process proceeds normally, without having to develop a new screen. Using system configuration table 565 greatly improves the flexibility and ease of reconfiguration for the high throughput screening systems disclosed herein. Alternatively, no configuration table is used. Instead, each device has a set of Cartesian coordinates associated therewith and the system is reprogrammed with a set of points that are associated with the device whenever equipment is moved. In this manner, the robots are optionally reprogrammed each time a new device is added at a particular location and defined station locations are not needed.

In one embodiment, a method is compiled once a screen has been completely identified by its method, plate set, and system variables. During the compiling process, the system controller preferably performs numerous quality checks on the method and utilized devices. For example, the compiler checks that the system has sufficient incubator capacity for the proposed method. Preferably, the compiler not only checks for circular, conflicting, or irrelevant step dependencies, but also optimizes the method by recognizing steps that can operate in parallel. The compiler also verifies all devices specified in the method are present in the system, and determines the station locations for each device. Accordingly, with the physical location of each device known, the required robotic motions are calculated and sequenced. If errors are found in the method, the operator is notified and the compilation optionally aborted.

Provided the method compiles properly, the screen is bundled into a schedule 475 that executes. For example, the schedule executes the appropriate method on the identified specimen plates and collects and reports data according to specific application needs. In addition, once the steps, methods, screens, and schedules are defined, they are optionally rearranged and reused, e.g., to facilitate the development of new schedules.

Still referring to FIG. 4, the software architecture also includes input-output control 465. The input-output control includes physical connections and logical communication to the individual instrument devices using instrument device drivers 505. It also includes network or other links back to the central system 515, and communications to the operator, which optionally include an operator console and operator alerts. The present inventions also typically provide input-output to other devices or systems. For example, the input-output control could provide imaging or printed output.

Software architecture 460 also contemplates that errors will arise on occasion within the screening systems. For convenience, errors are classified as hard errors 570 or soft errors 580 as shown in block 500. For example, soft errors can occur when a robotic gripper fails to couple to a specimen plate after three tries. Other soft errors may include low fluids in fluid-handling devices, and humidity or temperature out of range in an incubator. In one embodiment, such soft error failures require the attention of an operator, but do not warrant halting the process or rejecting one or more specimen plates. Therefore, upon detecting a soft error, the system preferably notifies an operator, such as by paging the operator according to paging or activating warning lights or audible signals using an operator alert.

However, the high throughput screening systems provided may also experience hard errors 570. Hard errors typically comprise major system failures such as a broken gripper, a failed robot, or any situation that substantially affects the process in operation. For example, a fluid well running dry or a critical error reported by one of the automated instrument devices would trigger a hard error. Upon detecting a hard error, the system preferably notifies the operator via paging or visual and audible alerts using an operator alert. Alternatively, the system rejects one or more specimen plates, and dispose of them, e.g., in a disposal station.

Preferably, the paging rules define an escalating order of operator notification. For example, the paging rules typically define that one or more junior operators be notified for soft errors, but that more senior operators or managers be notified upon a hard failure. In another example, the paging rules include time dependencies so that if an operator does not respond within a given time period, then another operator is paged. Paging rules are optionally adjusted and configured according to specific application requirements.

Figure 7:
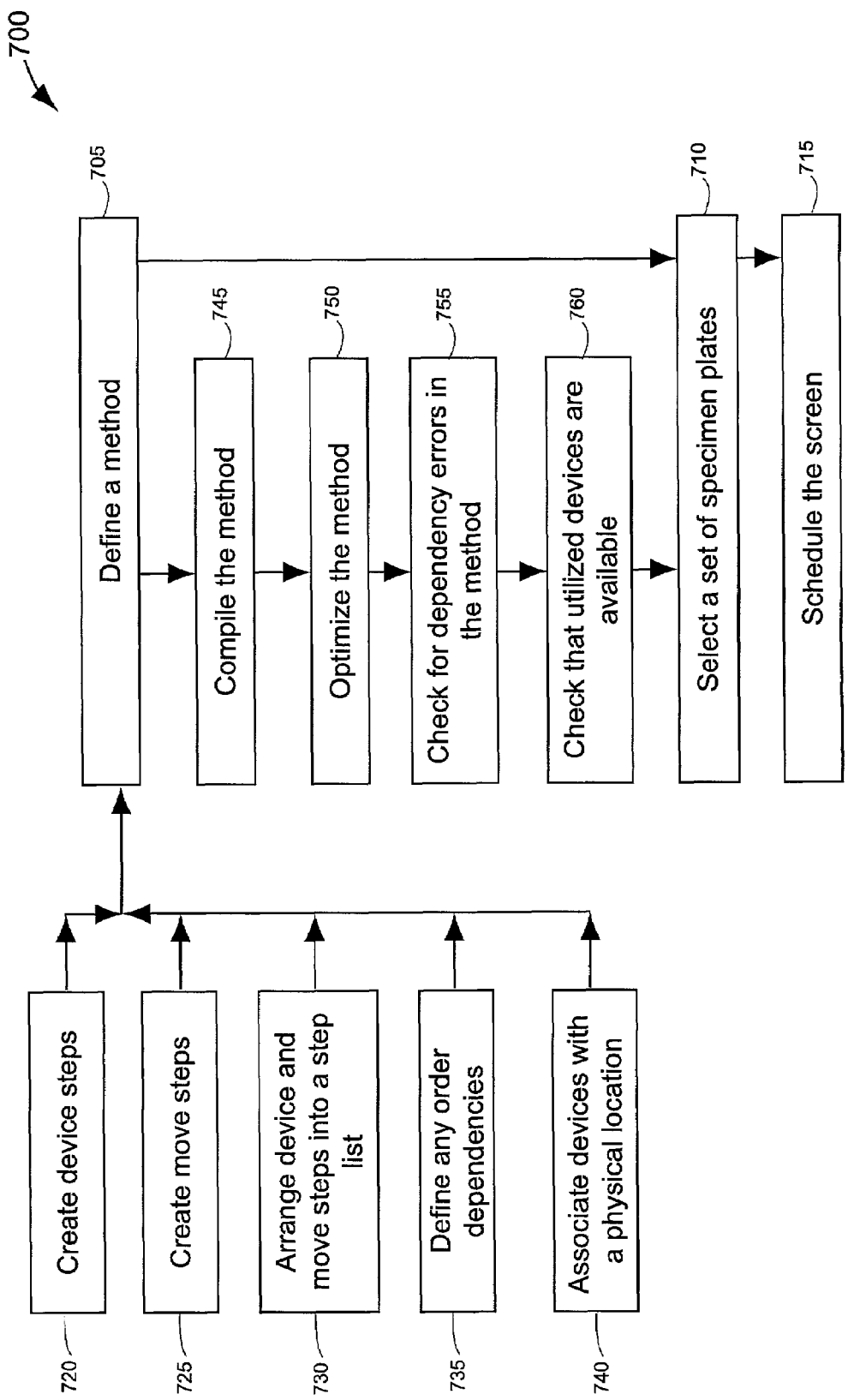
FIG. 7 is a block diagram illustrating a method of defining a screen in accordance with the present invention.

Referring now to FIG. 7, a method of defining a screening process, 700 is shown. Generally, defining a screen includes defining a process method 705, selecting a set of specimen plates 710 on which to operate the defined method, and scheduling the screen 715.

As shown in FIG. 7, the method in block 705 is defined by creating device steps 720, creating move steps 725, and arranging the device and move steps into a step list 730. Block 735 defines any order dependencies. Block 740 associates specific devices with their respective station locations. Alternative steps are optionally used in defining the method of block 705. After the method has been defined in block 705, the method is optionally compiled as shown in block 745. Compiling the method typically includes optimizing the method for more efficient operation as shown in block 750.

Further, compiling preferably checks for dependency errors 755, such as circular, redundant, and irrelevant dependencies. Also, compiling typically includes checking that all utilized devices are available in the system as in block 760. Preferably, the method of defining a screen 700 provides a modular and hierarchical method of defining screens. Advantageously, the present invention develops efficient screens, provides reusable methods, and easily reconfigures or scales high throughput systems to meet changing production requirements.

By using the above methods of designing processes and/or screens, large amounts of compounds are optionally tested in a relatively short period of time with accuracy, reliability, and efficiency. For example, about 500,000 samples are optionally processed in about 1 day to about 4 days. Example processes designed as described above, e.g., for use with the systems described above are detailed below.

B. Example Screening Processes

In one embodiment, a combination of analytical devices, such as dispensing devices, incubators, and detectors are installed in various station locations, each device preferably correlating to a unique and individual logical identifier. Multiwell specimen plates such as 1,536 well plates are processed robotically and in an automated fashion, although any size specimen plate is optionally used. In a particular example, a T-cell activation antagonist screen is performed. A dispensing device robotically plates Jurkat cells in specimen plates at a rate of about one to two minutes per plate. Once robotically transported to another workstation, another dispensing device dispenses about 50 µl of liquid into the specimen plates. After subsequent dispensing steps and an incubation step, a detector analyzes the specimen plates. Using this method, about 7000 compounds are optionally screened for T-cell activation in about 70 minutes. This embodiment further illustrates the integration of commercially available analytical devices into the present invention in order to easily and conveniently reap the benefits of all the aforementioned advantages. Example protocols are provided below.

Loading Plates into Hotel

Typically, an operator loads a plate storage area with micro-plates that contain the test compounds. The operator then typically inputs, e.g., to the supervisor PC, a protocol to load the plates into an appropriate incubator or compound storage hotel. The robot individually unloads plates from the plate storage area and loads them into the appropriate incubator or other compartment, e.g., storage compartments 910 and 912 in FIG. 9. The robot associated with that work perimeter scans all the bar codes on the plates to be loaded, and the hotel locations of the plates.

Plate Replication

Empty target plates are loaded, e.g., into a first plate storage area in work perimeter 940, again referring to FIG. 9. The operator writes the protocol and lists specific library plates to be replicated. The robot in work perimeter 902 unloads a compound plate from the hotel and loads it onto the table of a 384 Hydra 928. The robot in work perimeter 940 removes an empty plate from the plate storage area to transfer station 983, from which the robot in work perimeter 920 moves it onto the table of a 384 Hydra workstation 928. The Hydra aspirates a pre-determined volume of DMSO from the wash reservoir and dispenses it into the empty (target) plate. The Hydra aspirates a pre-determined volume of compound from the source plate and dispenses it into the target plate. The source and target plates are removed from the 384 Hydra and loaded back onto the appropriate incubators or hotels such as, for example incubators 910 and 912 in work perimeter 902.

Compound Picking

The operator enters, e.g., into the supervisor PC, the specific compounds and volumes to be retrieved from the library. Empty multiwell plates are loaded into an incubator 930, referring to FIG. 9. The robot scans all the bar codes on the plates and the hotel locations to verify the location and presence of these target plates. The robot in work perimeter 920 unloads an empty plate from the hotel and loads it onto the Cartesian liquid handler 932. The robot in work perimeter 902 removes the appropriate compound plate from a hotel on the dial and loads it onto transfer station 918. The robot in work perimeter 920 removes the plate from the transfer station and loads it onto the Cartesian liquid handler.

The Cartesian aspirates a pre-determined volume of fluid from the correct well(s) of the compound plate and transfers the fluid to the target multiwell plate. The compound (source plate) is removed from the Cartesian and loaded back onto the transfer station 918. The compound plate is removed from the transfer station by robot 916 and loaded back into the appropriate hotel or incubator. After the desired number of target compounds have been picked (or the protocol completed), the target multiwell plate is unloaded from the Cartesian and loaded into a hotel or other plate storage area (e.g., incubator 912) for further use.

Dispensing Cells 1536 well assay plates are loaded into the incubator 930. Robot 936 removes the empty 1536 well assay plate from the incubator and positions it onto the Cartesian 932. Cells are dispensed into the wells of the 1536 well assay plate, e.g., with an approximately 30 second cycle time. Robot 936 unloads the plate from the Cartesian and places it back into the incubator. The process is optionally repeated for all 135 plates.

Adding Compound

In this embodiment, about 540 compound plates are present in the library plate hotel. Robot 916 loads a library plate from the library hotel to the Hydra 96 Ultra 928, which functions as a transfer station between work perimeter 902 and work perimeter 920. Robot 936 removes a 1536 well assay plate (with cells) from the incubator 930 and loads it onto the Hydra 96 Ultra 928. Fluid is aspirated 4 times, e.g., using the 96-dispenser head, from the 384 compound plate and dispensed into the 1536 well assay plate (it takes approximately 3 min to complete 4 washes and 4 aspirate and dispenses). Robot 936 removes the assay plate from the Hydra and loads it back into the incubator 930. Robot 916 removes the compound plate from the Hydra and loads it back into the library hotel 912. Typically, robots 936 and 916 load a total of 135 assay plates and 540 compound plates into and out of the Hydra 96 Ultra.

Incubation

Assay plates are typically incubated for about 4 hours (plus or minus 10%), e.g., prior to being removed for imaging. Therefore, plates are typically being moved to the readers while compounds are being dispensed into assay plates.

Dispensing Reagent and Plate Reading

A 1536 well assay plate is removed from the incubator 930 and loaded into the Cartesian 932. One or more reagent is dispensed into each of the 1536 wells in the assay plate (approx 45 seconds). Robot 936 removes the plate from the Cartesian and loads it onto the material handling dial 983. The material handling dial transports the assay plate from work perimeter 920 to work perimeter 940. The robot in work perimeter 940 removes the plate from the transfer station (which, in this case, is a material handling dial) and loads it into the plate reader 948. Plates are preferably loaded to the reader in less than about 30 seconds after dispensing of reagent. The plate is read (approx 5 minutes). After the plate is read, robot 946 removes the plate from the incubator and loads it back on the material handling dial. The material handling dial transports the plate from work perimeter 940 to work perimeter 920. The robot in work perimeter 920 to returns the completed assay plate to the incubator. The process is typically repeated for each of about 135 assay plates.

When kinetic plate reading is desired, the robot optionally returns the plates to the plate reader after additional incubation times. For example, robot 936 removes the plate from the incubator and loads it into a hotel in work perimeter 940. After 30 minutes robot 946 removes the plate from the hotel in work perimeter 940 and loads it back into the plate reader 948. The plate is read (approx 1 minute). After the plate is read, robot 946 removes the plate from the incubator and loads it into the hotel in work perimeter 940. After an additional 30 minutes, robot 946 removes the plate from the hotel in work area 940 and loads it back into the plate reader. The plate is read (approx 1 minute). After the plate is read, robot 946 removes the plate from the plate reader and loads it back on the material handling dial 983. The material handling dial transports the plate from cell work perimeter 940 to work perimeter 920.

Dispensing Equipment Process Development

The operator typically writes a protocol to dispense 5 µl of cells into one 1536 well plate and then manually loads one or more 1536 well microplates onto the table comprising a Cartesian workstation, which automatically dispenses cells into wells of 1536 well plate. The operator optionally manually removes the plate and visually inspects it. The plate is then typically manually loaded into a plate reader, which reads the plate. The plate is then typically removed, e.g., manually.

One skilled in the art will appreciate that the present invention can be practiced by other than the embodiments which are presented in this description for purposes of illustration and not of limitation, and the present invention is limited only by the claims which follow. It is noted that equivalents for the particular embodiments discussed in this description may practice the invention as well.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations and other uses for the present invention are also contemplated. In particular, other high throughput processes may utilize the present invention. Also, the present invention is optionally employed to assemble electronic devices, medical devices, or other devices that require multiple assembly steps. In addition, the present invention can be used to perform medical testing, chemical synthesis, or any other multiple process procedure.

All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A high throughput processing system, the system comprising:
   (a) a plurality of rotational robots, wherein each of the rotational robots has a reach which defines a work perimeter associated with that rotational robot, wherein at least one of the rotational robots comprises a grasping mechanism that comprises moveably coupled arms that are structured to grasp an object, wherein at least one arm comprises a pivot member having a support surface to support the object and a height adjusting surface that pushes the object into contact with the support surface when the arms grasp the object;
   (b) at least one device associated with each of the rotational robots and the associated work perimeters; and,
   (c) one or more transfer stations, wherein each transfer station is associated with two work perimeters.

2. The high throughput processing system of claim 1, wherein the system further comprises one or more storage modules associated with at least one of the rotational robots and the associated work perimeter, wherein the storage modules provide storage capacity for a plurality of test samples.

3. The high throughput processing system of claim 2, wherein the plurality of test samples in the storage modules comprise chemical or biochemical compounds, nucleic acids, peptides, polypeptides, proteins, carbohydrates, cells, serum, phage particles, virions, enzymes, cell extracts, lipids, or antibodies.

4. The high throughput processing system of claim 3, wherein the test samples comprise a library of cDNA molecules.

5. The high throughput processing system of claim 3, wherein the test samples comprise a library of gene regulatory regions operably linked to a reporter gene.

6. The high throughput processing system of claim 5, wherein the regulatory regions in the library are derived from genes that are differentially expressed in a cell depending upon the presence or absence of a particular stimulus.

7. The high throughput processing system of claim 3, wherein the test samples comprise a library of antisense nucleic acids or double-stranded RNA molecules.

8. The high throughput processing system of claim 3, wherein the test samples comprise a combinatorial library of chemical compounds.

9. The high throughput processing system of claim 2, wherein the at least one device associated with one of the rotational robots and associated work perimeter comprises one or more incubators for incubating the assay containers.

10. The high throughput processing system of claim 9, wherein the assay containers comprise one or more components of an assay, and a test sample is added to the assay containers to determine the effect of the test samples on the assay.

11. The high throughput processing system of claim 10, wherein the assay is selected from the group consisting of a G-protein coupled receptor assay, a kinase assay, a protease assay, a phosphatase assay, and a transcription assay.

12. The high throughput processing system of claim 10, wherein the assay is a cell-based assay.

13. The high throughput processing system of claim 2, wherein the plurality of test samples comprise one or more of specimen plates, multiwell plates, petri dishes, test tube arrays, vials, crucibles, flasks, reaction vessels, or slides.

14. The high throughput processing system of claim 13, wherein the plurality of test samples comprise one or more of 1536-well plates, 384-well plates, or 96-well plates.

15. The high throughput processing system of claim 14, wherein a first work perimeter comprises a storage module that contains 384-well plates and a second work perimeter comprises an incubator that contains 1536-well plates.

16. The high throughput processing system of claim 2, wherein the system further comprises sample holders and one or more sample holder lids.

17. The high throughput processing system of claim 16, wherein the sample holders are multiwell plates and the lids comprise:
- a cover having a top surface, a bottom surface, and a side;
- an alignment protrusion extending from the side of the cover, the alignment protrusion positioned to cooperate with an alignment member of the multiwell plate;
- a sealing perimeter positioned on the bottom surface of the cover; and
- wherein the alignment protrusion facilitates aligning the lid to the plate so that a seal is compressibly received between the sealing perimeter and a sealing surface of the multiwell plate.

18. The high throughput processing system of claim 16, wherein one or more of the work perimeters comprises a de-lidding station at which a lid is removed from a sample holder.

19. The high throughput processing system of claim 16, wherein the lid is constructed from stainless steel.

20. The high throughput processing system of claim 1, wherein the rotational robots each comprise one or more grippers configured to transport the sample holders.

21. The high throughput processing system of claim 20, wherein the gripper comprises a sensor structured to determine a location of the gripper apparatus relative to the object.

22. The high throughput processing system of claim 20, wherein the gripper comprises a deflectable member structured to couple the gripper apparatus to a robotic member, which deflectable member is structured to deflect when the gripper apparatus contacts an item with a force greater than a preset force.

23. The high throughput processing system of claim 1, wherein at least one of the transfer stations comprises a first pin tool and, wherein a transfer station other than the at least one transfer station comprising the first pin tool transfers the one or more samples by transferring a sample holder from the first or second work perimeter to another work perimeter.

24. The high throughput processing system of claim 1, wherein the rotational robots are configured to transport one or more sample holders along a multi-directional path.

25. The high throughput processing system of claim 1, wherein the system comprises between 2 and 10 rotational robots.

26. The high throughput processing system of claim 1, wherein the devices associated with each of the work perimeters are independently selected from the group consisting of: a fluid transfer device, a mixer, an incubator, a storage compartment, a thermocycler, a plate carousel, an automatic sample processor, a detector, and a replating station.

27. The high throughput processing system of claim 26, wherein one or more of the devices comprise a fluid transfer device.

28. The high throughput processing system of claim 27, wherein the fluid transfer device comprises an apparatus selected from the group consisting of: a pin tool, a syringe, and a pump.

29. The high throughput processing system of claim 28, wherein at least one of the sample holders is a multiwell plate and the fluid transfer device is a pin tool that comprises an array of pins that are aligned with a plurality of wells of the multiwell plate.

30. The high throughput processing system of claim 29, wherein the pin tool further comprises one or more wash stations in which the pins are washed between transfers of fluid from one multiwell plate to another by the pin tool.

31. The high throughput processing system of claim 27, wherein at least one of the sample holders is a multiwell plate and the fluid transfer device further comprises an array of receptacles arranged such that outlets of the receptacles are aligned with a plurality of wells of the multiwell plate.

32. The high throughput processing system of claim 31, wherein the fluid transfer device comprises 96 or 384 receptacles.

33. The high throughput processing system of claim 31, wherein the receptacles are syringes.

34. The high throughput processing system of claim 31, wherein the fluid transfer device:
- aspirates a volume of sample into one or more of the receptacles from a well of a multiwell plate which is aligned with the outlet of the receptacle;
- returns a substantial portion of the volume of the aspirated sample to the well of the multiwell plate, the returned volume of the liquid being less than the aspirated volume so that a volume of sample is retained in the receptacle;
- dispenses a portion of the retained volume of sample into a well of a second multiwell plate; and
- discards any remaining volume of retained liquid.

35. The high throughput processing system of claim 34, wherein the volume of the aspirated sample is at least several times the volume of dispensed sample.

36. The high throughput processing system of claim 27, wherein the fluid transfer device does not comprise disposable pipette tips.

37. The high throughput processing system of claim 36, wherein no fluid transfer device in the system comprises disposable pipette tips.

38. The high throughput processing system of claim 27, wherein the fluid transfer device comprises a positive displacement pump coupled to a dispenser valve.

39. The high throughput processing system of claim 26, wherein one or more of the devices comprises an incubator or storage compartment.

40. The high throughput processing system of claim 39, wherein the system comprises storage compartments that provide storage capacity for at least 350,000 samples.

41. The high throughput processing system of claim 40, wherein the storage compartments provide storage capacity for at least 700,000 samples.

42. The high throughput processing system of claim 41, wherein the storage compartments provide storage capacity for at least 1,400,000 samples.

43. The high throughput processing system of claim 39, wherein the incubator or storage compartment comprises:
- (a) a housing comprising a plurality of doors, which doors close at least one opening disposed through at least one surface of the housing;
- (b) at least one movable shelf disposed within the housing, which shelf is capable of aligning with the opening;
- wherein each of the plurality of doors is independently accessible by the rotational robot.

44. The high throughput processing system of claim 26, wherein one or more of the devices comprises a detector which detects one or more readouts of assay results.

45. The high throughput processing system of claim 44, wherein the detector comprises a device selected from the group consisting of a fluorescence detector, a spectrophotometric detector, a luminescence detector, a phosphorescence detector, an X-ray detector, a radio-frequency detector, a bar code reader, a mass spectrometer, a radioactivity detector, and an optical detector.

46. The high throughput processing system of claim 44, wherein the detector comprises a camera which records images of the assay results.

47. The high throughput processing system of claim 46, wherein the images are digital images.

48. The high throughput processing system of claim 46, wherein the images are analyzed to determine assay results which indicate a desired effect of a test sample.

49. The high throughput processing system of claim 1, wherein one or more of the devices comprises an automatic sample processor.

50. The high throughput processing system of claim 1, wherein the system can perform assays of at least 100,000 samples in one day.

51. The high throughput processing system of claim 50, wherein the system can perform assays of at least 350,000 samples in one day.

52. The high throughput processing system of claim 51, wherein the system can perform assays of at least 700,000 samples in one day.

53. The high throughput processing system of claim 1, wherein one or more of the devices comprises a positioning device that comprises at least a first alignment member that is positioned to contact an inner wall of a multiwell plate when the multiwell plate is in a desired position on the device.

54. The high throughput processing system of claim 53, wherein the positioning device further comprises a pusher that can move the multiwell plate in a first direction to bring at least a first inner wall of the multiwell plate into contact with one or more of the alignment members.

55. The high throughput processing system of claim 54, wherein the positioning device further comprises a second pusher that can move the multiwell plate in a second direction to bring a second inner wall of the multiwell plate into contact with one or more alignment members that are positioned to contact the second inner wall of the multiwell plate when the multiwell plate is in a desired position on the device.

56. The high throughput processing system of claim 1, wherein the controller is operably coupled to one or more of the rotational robots.

57. The high throughput processing system of claim 56, wherein the controller directs transport of the sample holders between one or more of the work perimeters or between one or more of the devices.

58. The high throughput processing system of claim 54, wherein said transport is non-sequential or non-linear transport.

59. The high throughput processing system of claim 56, wherein the controller is configured to receive operator instructions and provide operator information.

60. The high throughput processing system of claim 59, wherein the operator instructions are received through a graphical user interface.

61. The high throughput processing system of claim 56, wherein a separate controller controls each rotational robot.

62. The high throughput processing system of claim 61, wherein the system further comprises an operator interface that receives operator instructions and provides operator information from each controller.

63. The high throughput processing system of claim 1, further comprising an operator alert operably coupled to the system.

64. The high throughput processing system of claim 63, wherein the operator alert comprises a visual alert, an audio alert, or a paging alert.

65. The high throughput processing system of claim 1, wherein the system comprises a first work perimeter directed to test sample storage and a second perimeter directed to performing an assay.

66. The high throughput processing system of claim 65, wherein the test samples comprise chemical compounds.

67. The high throughput processing system of claim 65, wherein the transfer station comprises a fluid transfer device that transfers an aliquot of a test sample from a sample holder that comprises test samples to an assay sample holder in which an assay is to be performed.

68. The high throughput processing system of claim 67, wherein the assay sample holder comprises one or more of living cells, cell extracts, nucleic acids, polypeptides, antibodies, or chemicals.

69. The high throughput processing system of claim 65, wherein the assay comprises one or more of a biochemical, chemical, biological, microbiological, or cell-based assay.

70. The high throughput processing system of claim 65, wherein the second work perimeter comprises an incubator for maintaining the assay sample holders in a desired environment.

71. The high throughput processing system of claim 65, wherein the system further comprises a detection device for collecting data from the assay.

72. The high throughput processing system of claim 71, wherein the detection device is located in the second work perimeter.

73. The high throughput processing system of claim 71, wherein the detection device is located in a third work perimeter.

* * * * *